US012590122B2

(12) United States Patent
Lepelletier et al.

(10) Patent No.: US 12,590,122 B2
(45) Date of Patent: Mar. 31, 2026

(54) NRP-1 BINDING INHIBITORY PEPTIDES AND USES THEREOF

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIWERSYTET WARSZAWSKI, Warsaw (PL); FONDATION IMAGINE, Paris (FR); ASSISTANCE PUBLIQUE—HÔPITAUX DE PARIS, Paris (FR); UNIVERSITE DE PARIS, Paris (FR)

(72) Inventors: Yves Lepelletier, Paris (FR); Françoise Raynaud, Paris (FR); Aleksandra Misicka-Kesik, Warsaw (PL); Anna Katarzyna Puszko, Warsaw (PL); Olivier Hermine, Paris (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIWERSYTET WARSZAWSKI, Warszawski (PL); FONDATION IMAGINE, Paris (FR); ASSISTANCE PUBLIQUE—HÔPITAUX DE PARIS, Paris (FR); UNIVERSITE DE PARIS, Paris (FR)

( * ) Notice: Subject to any disclaimer, the term of this patent is extended or adjusted under 35 U.S.C. 154(b) by 1143 days.

(21) Appl. No.: 17/618,233

(22) PCT Filed: Jun. 10, 2020

(86) PCT No.: PCT/EP2020/066062

§ 371 (c)(1),
(2) Date: Dec. 10, 2021

(87) PCT Pub. No.: WO2020/249605

PCT Pub. Date: Dec. 17, 2020

(65) Prior Publication Data

US 2022/0169677 A1 Jun. 2, 2022

(30) Foreign Application Priority Data

Jun. 13, 2019 (EP) .................................... 19305756

(51) Int. Cl.

| | |
|---|---|
| ***C07K 7/02*** | (2006.01) |
| ***C07K 5/02*** | (2006.01) |
| ***C07K 5/11*** | (2006.01) |
| ***C07K 7/06*** | (2006.01) |
| *A61K 38/00* | (2006.01) |

(52) U.S. Cl.
CPC .......... *C07K 5/1019* (2013.01); *C07K 5/0215* (2013.01); *C07K 7/02* (2013.01); *C07K 7/06* (2013.01); *A61K 38/00* (2013.01)

(58) Field of Classification Search
CPC ...... C07K 5/1019; C07K 5/0215; C07K 7/02; C07K 7/06; A61K 38/00
See application file for complete search history.

(56) References Cited

FOREIGN PATENT DOCUMENTS

| | | | |
|---|---|---|---|
| WO | 2006/130504 | A2 | 12/2006 |
| WO | 2015/026251 | A2 | 2/2015 |

OTHER PUBLICATIONS

Naim et al, Immunological Investigations, 1991, 20(4), 351-64 (Year: 1991).*
Starzec A et al: "Antiangiogenic and antitumor activities of peptide inhibiting the vascular endothelial growth factor binding to neuropilin-1", Life Sciences, Pergamon Press, Oxford, GB, vol. 79, No. 25, Nov. 17, 2006 (Nov. 17, 2006) , pp. 2370-2381.
Tymecka Dagmara et al: "Structure-activity relationship study of tetrapeptide inhibitors of the Vascular Endothelial Growth Factor A binding to Neuropilin-1", Peptides, Elsevier, Amsterdam, NL, vol. 94, Jun. 13, 2017 (Jun. 13, 2017), pp. 25-32.
Dagmara Tymecka et al: "Branched pentapeptides as potent inhibitors of the vascular endothelial growth factor 165 binding to Neuropilin-1: Design, synthesis and biological activity", European Journal of Medicinal Chemistry, vol. 158, Oct. 1, 2018 (Oct. 1, 2018), pp. 453-462.
Bartlomiej Fedorczyk et al: "triazolopeptides Inhibiting the Interaction between Neuropilin-1 and Vascular Endothelial Growth Factor-165", Molecules Online, vol. 24, No. 9 , May 6, 2019 (May 6, 2019), p. 1756.

* cited by examiner

*Primary Examiner* — Sudhakar Katakam
(74) *Attorney, Agent, or Firm* — WCF IP

(57) ABSTRACT

A number of anti-angiogenic strategies connected with the VEGF signalling pathway are used in current clinical treatment or trial phase, but they either cause adverse effects or are not specific. Various strategies were aimed at identifying peptides inhibiting the VEGF-$A_{165}$/NRP-1 interaction. A well-known antiangiogenic peptide is the heptapeptide termed "A7R" having the amino acid sequence ATWLPPR, for which various derivatives have been synthesized, which include peptides having the general sequence Lys(hArg)-$AA^2$-$AA^3$-Arg. However, the ability of the known peptides to inhibit the VEGF-$A_{165}$/NRP-1 interaction was too low for their use as candidate drugs for inhibiting angiogenesis in subjects in need thereof. The present inventors have now conceived a family of novel peptide-like compounds having a nanomolar affinity for NRP-1, which are thus endowed with a powerful capacity to inhibit the VEGF-$A_{165}$/NRP-1 interaction. These novel peptide-like compounds may be relevantly used as antiangiogenic compounds, especially in subjects affected with cancer.

15 Claims, No Drawings

Specification includes a Sequence Listing.

NRP-1 BINDING INHIBITORY PEPTIDES AND USES THEREOF

FIELD OF THE DISCLOSURE

The present disclosure relates to the field of VEGF inhibitors for medical use and more precisely to the field of peptide inhibitors of the VEGF-$A_{165}$/NRP-1 interaction.

BACKGROUND OF THE DISCLOSURE

Neuropilin-1 (also termed "NRP-1") is overexpressed in various kinds of malignant tumors. The interaction of NRP-1 with the vascular endothelial growth factor 165 (also termed "VEGF-$A_{165}$") leads to the progression of tumor vascularization and growth. NRP-1 is a co-receptor for tyrosine kinase receptor VEGF-R1/VEGF-R2/VEGF-R3 and their signalling are critical for lymphoangiogenesis, angiogenesis and tumor growth.

A number of anti-angiogenic strategies connected with the VEGF signalling pathway are used in current clinical treatment or trial phase, but they either cause adverse effects or are not specific (Papadopoulos et al., 2012, Angiogenesis, Vol. 15: 171-185).

With the view of treating diseases involving an interaction between NRP-1 and VEGF-$A_{165}$, compounds have been identified in the art that alter or block this interaction.

Notably, a class of peptides that share a R/K/XXR/K motif with the C-terminal domain of VEGF-$A_{165}$ and bind to NRP-1 have been selected through a phage display screening method (Teesalu et al., 2009, Proc Natl Acad Sci USA, Vol. 106 (39): 16157-16162).

A well-known peptide that blocks the interaction of NRP-1 with VEGF-$A_{165}$ is the heptapeptide termed "A7R" having the amino acid sequence ATWLPPR (SEQ ID NO. 1) (Binetruy-Tournaire et al., 2000, EMBO J, Vol. 19: 1525-1533). Basing on the shortest active sequence (LPPR) of A7R (Starzec et al., 2007, Peptides, Vol. 28: 2397-2402), a new family of peptides were developed which exhibit a significant VEGF-$A_{165}$/NRP-1 binding inhibitory effect (Fedorczyk et al., 2017, J Pept Sci, Vol. 23: 445-454; Tymecka et al., 2018, Eur J Med Chem, Vol. 158: 453-462). The most active of these peptides have the general sequence Lys (hArg)-$AA^2$-$AA^3$-Arg (SEQ ID NO. 2), where $AA^2$ or $AA^3$ are Proline residues (Tymecka et al., 2018, Eur J Med Chem, Vol. 158: 453-462). These authors have shown that some of the peptides having the general sequence Lys(hArg)-$AA^2$-$AA^3$-Arg allow a more effective inhibition, the most active compounds being over 23-fold more potent than the parent peptide KPPR and the heptapeptide A7R which was proved to have antiangiogenic activity in vivo.

Other peptides of the general sequence Lys(hArg)-$AA^2$-$AA^3$-Arg were further conceived and tested for their VEGF-$A_{165}$/NRP-1 binding inhibitory effect (Puszko et al., 2019, MedChemComm, Vol. 10: 332-340). These authors have synthesized a plurality of series of peptides comprising multiple variations in $AA^2$ and $AA^3$, respectively, by replacing the initial proline residues by unnatural proline analogues with different rigidity and ring size, such as those termed Hyp, Aze, ΔPro, Oic, Piz and Tic, respectively. The results showed that optimization of the central part of the parent sequence (i.e. $AA^2$ and $AA^3$ residues) led to compounds, which show a 2- and 4-fold decrease in the $IC_{50}$. According to these authors, replacing the initial proline residue located as $AA^3$ by ΔPro or Oic seemed to increase interaction with NRP-1. These authors believed that this increased binding to NRP-1 might probably due to the more rigid rings in ΔPro and Oic, which might promote the optimal peptide-like chain position on the receptor surface.

There remains a need for further compounds altering or blocking the VEGF-$A_{165}$/NRP-1 interaction so as to generate an antiangiogenic and/or anti-tumoral activities that is useful in the treatment of diseases such as cancers.

SUMMARY

The present disclosure relates to a compound of formula (I)

(I)

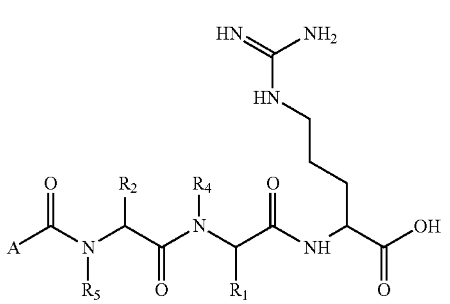

wherein, for groups R1 and R4, a) R1 is a group of formula (LC1)

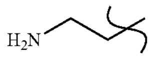

and R4 is H, or b) R1 and R4, together with the carbon and nitrogen atoms to which they are linked, form a pyrrolidinyl ring, or c) R1 and R4, together with the carbon and nitrogen atoms to which they are linked, form a 2,5-dihydro-1-H-pyrrolyl ring, or d) R1 and R4, together with the carbon and nitrogen atoms to which they are linked, form a octahydro-1H-indolyl ring, or e) R1 is a group of formula (LC2)

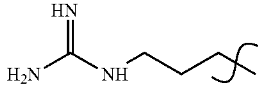

and R4 is H, for groups R2 and R5, a) R2 is a group of formula (LC3)

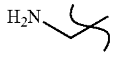

and R5 is H, or b) R2 is a group of formula (LC1)

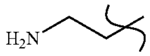

and R5 is H, or c) R2 and R5, together with the carbon and nitrogen atoms to which they are linked, form a pyrrolidinyl ring, or d) R2 and R5, together with the carbon and nitrogen atoms to which they are linked, form a 2,5-dihydro-1-H-pyrrolyl ring, or e) R2 and R5, together with the carbon and nitrogen atoms to which they are linked, form a octahydro-1H-indolyl ring, or f) R2 is a group of formula (LC2)

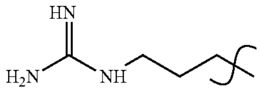

and R5 is H, or g) R2 is a group of formula (LC4)

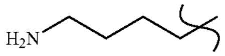

and R5 is H,

A is selected in the group of formulas A1 and A2 below:

wherein A1 is of the formula below:

(A1)

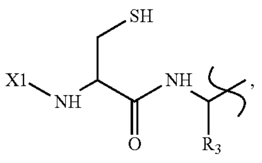

wherein X1 is selected in the group consisting of H, —C(═O)—CH3 and an amine protecting group, and wherein R3 is selected in the group consisting of a) R3 is a group of formula (LC4)

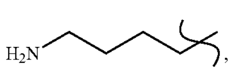

or b) R3 is a group of formula (LC5)

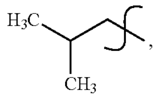

or c) R3 is a group of formula (LC6)

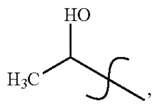

or d) R3 is a group of formula (LC7)

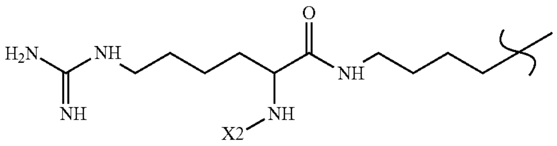

and wherein X2 is selected in the group consisting of H, —C(═O)—CH3 and an amine protecting group, and and wherein A2 is of the formula below:

(A2)

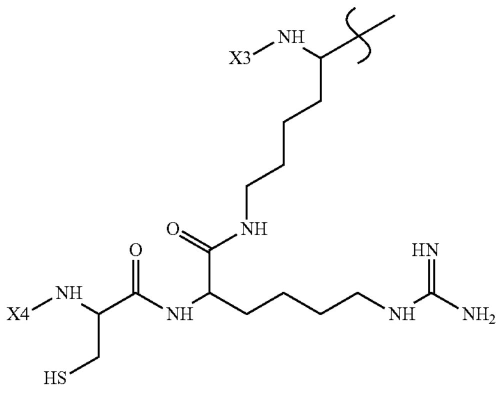

wherein X3 and X4, which are identical or different, are selected in the group consisting of H, —C(═O)—CH3 and an amine protecting group, provided that the compound of formula (I) does not consist of the peptide CKPPR, and any pharmaceutically acceptable salts and/or racemic, enantiomeric, diastereoisomeric or tautomeric forms thereof of the compound of formula (I).

In some embodiments, the compound of formula (I) is selected in a group comprising (i) H-Cys-Lys(hArg)-Dab-ΔPro-Arg-OH, (ii) H-Lys(Cys-hArg)-Dab-ΔPro-Arg-OH, (iii) H-Cys-Lys(hArg)-Dab-Oic-Arg-OH and (iv) H-Lys(Cys-hArg)-Dab-Oic-Arg-OH which are the compounds of respective formulae (I-A), (I-B), (I-C) and (I-D) described in the present disclosure.

This disclosure further relates to a compound of formula (I) for its use for preventing or treating a diseased subject in need of an angiogenesis inhibitor.

This disclosures further pertains relates to a compound of formula (I) for its use for preventing or treating in a subject.

DETAILED DESCRIPTION OF THE DISCLOSURE

The inventors have conceived novel VEGF-$A_{165}$/NRP-1 inhibitors having outstanding properties as compared with the already known peptide inhibitors derived from the parent peptide KPPR (A7R active sequence), TKPR (tuftsin) and KPRR (VEGF-$A_{165}$ C-terminal sequence).

More precisely, the inventors have conceived peptides comprising a cysteine residue at their N-terminal end that far more efficiently bind to NRP-1, and thus block the VEGF-$A_{165}$/NRP-1 interaction than the peptides already known in the art.

The present inventors have shown that the improved peptides that they have conceived totally unexpectedly bind to NRP-1 at the nanomolar level, as compared with the most efficient of the known peptides that bind NRP-1 at the micromolar level.

Compounds of the Disclosure

Then, the present disclosure relates to a compound of formula (I)

(I)

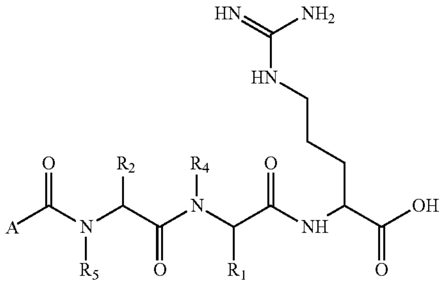

wherein, for groups R1 and R4, a) R1 is a group of formula (LC1)

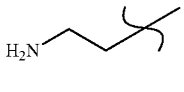

and R4 is H, or b) R1 and R4, together with the carbon and nitrogen atoms to which they are linked, form a pyrrolidinyl ring, or c) R1 and R4, together with the carbon and nitrogen atoms to which they are linked, form a 2,5-dihydro-1-H-pyrrolyl ring, or d) R1 and R4, together with the carbon and nitrogen atoms to which they are linked, form a octahydro-1H-indolyl ring, or e) R1 is a group of formula (LC2)

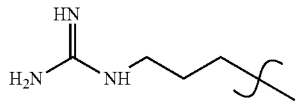

and R4 is H.

for groups R2 and R5, a) R2 is a group of formula (LC3)

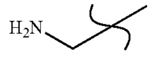

and R5 is H, or b) R2 is a group of formula (LC1)

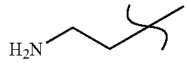

and R5 is H, or c) R2 and R5, together with the carbon and nitrogen atoms to which they are linked, form a pyrrolidinyl ring, or d) R2 and R5, together with the carbon and nitrogen atoms to which they are linked, form a 2,5-dihydro-1-H-pyrrolyl ring, or e) R2 and R5, together with the carbon and nitrogen atoms to which they are linked, form a octahydro-1H-indolyl ring, or f) R2 is a group of formula (LC2)

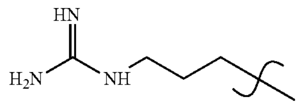

and R5 is H, or g) R2 is a group of formula (LC4)

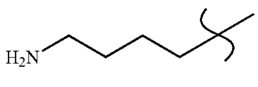

and R5 is H.

A is selected in the group of formulas A1 and A2 below:

wherein A1 is of the formula below:

(A1)

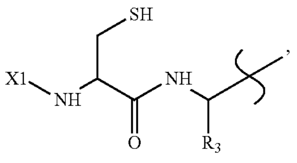

wherein X1 is selected in the group consisting of H, —C(═O)—CH3 and an amine protecting group, and wherein R3 is selected in the group consisting of a) R3 is a group of formula (LC4)

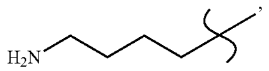

or b) R3 is a group of formula (LC5)

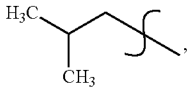

or c) R3 is a group of formula (LC6)

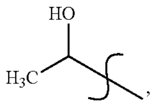

or d) R3 is a group of formula (LC7)

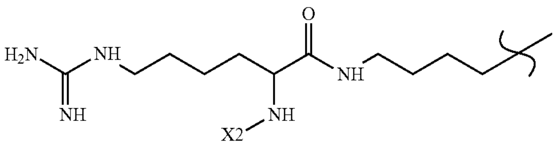

and wherein X2 is selected in the group consisting of H, —C(═O)—CH3 and an amine protecting group, and and wherein A2 is of the formula below:

(A2)

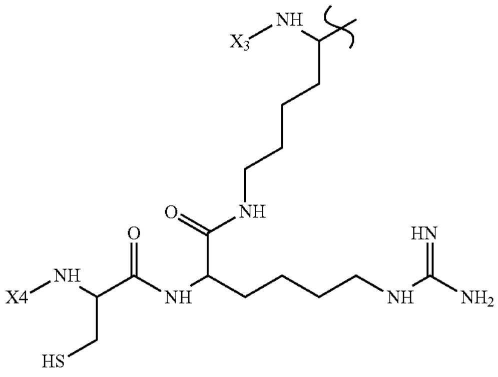

wherein X3 and X4, which are identical or different, are selected in the group consisting of H, —C(═O)—CH3 and an amine protecting group, provided that the compound of formula (I) does not consist of the peptide CKPPR, and any pharmaceutically acceptable salts and/or racemic, enantiomeric, diastereoisomeric or tautomeric forms thereof of the compound of formula (I).

For the sake of clarity, none of the compounds according to the present disclosure may consist of the peptide CKPPR. It is specified that the peptide CKPPR is disclosed in the PCT application published under n° WO 2006/130504. This patent application disclosed methods for identifying ligands for stem cells and for cells derived therefrom, and thus belongs to a technical field which is remote from that of the present disclosure.

Unless otherwise indicated, any chemical group specified in the present disclosure is non-substituted.

In embodiments of a compound of formula (I) wherein R1 is a group of formula (LC1)

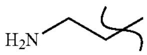

and R4 is H, then the corresponding residue consists of a 2,4-diaminobutyric acid (also termed "Dab").

In embodiments of a compound of formula (I) wherein R1 and R4, together with the carbon and nitrogen atoms to which they are respectively linked, form a pyrrolidine ring, then the corresponding residue consists of a proline (also termed "Pro").

In embodiments of a compound of formula (I) wherein R1 and R4, together with the carbon and nitrogen atoms to which they are respectively linked, form a 2,5-dihydro-1-H-pyrrolyl, then the corresponding residue consists of a 3,4-dehydroproline (also termed ΔPro").

In embodiments of a compound of formula (I) wherein R1 and R4, together with the carbon and nitrogen atoms to which they are respectively linked, form a octahydroindolyl ring, then the corresponding residue consists of a octahydro-1H-indole-2-carboxylic acid (also termed "Oic").

In embodiments of a compound of formula (I) wherein R1 is a group of formula (LC2)

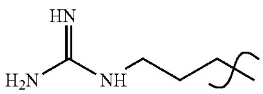

and R4 is H, then the corresponding residue consists of an arginine (also termed "Arg").

In embodiments of a compound of formula (I) wherein R2 is a group of formula (LC3)

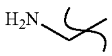

and R5 is H, then the corresponding residue consists of 2,3-diaminopropionic acid (also termed "Dap").

In embodiments of a compound of formula (I) wherein R2 is a group of formula (LC1)

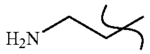

and R5 is H, then the corresponding residue consists of 2,4-diaminobutyric acid (also termed "Dab").

In embodiments of a compound of formula (I) wherein R2 and R5, together with the carbon and nitrogen atoms to which they are respectively linked, form a pyrrolidine ring, then the corresponding residue consists of proline (also termed "Pro").

In embodiments of a compound of formula (I) wherein R2 and R5, together with the carbon and nitrogen atoms to which they are linked, form a 2,5-dihydro-1-H-pyrrolyl, then the corresponding residue consists of a 3,4-dehydro-proline (also termed "ΔPro").

In embodiments of a compound of formula (I) wherein R2 and R5, together with the carbon and nitrogen atoms to which they are respectively linked, form a octahydroindolyl ring, then the corresponding residue consists of an octa-hydro-1H-indole-2-carboxylic acid (also termed "Oic").

In embodiments of a compound of formula (I) wherein R2 is a group of formula (LC2)

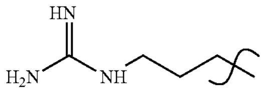

and R5 is H, then the corresponding residue consists of arginine (also termed "Arg").

In embodiments of a compound of formula (I) wherein R2 is a group of formula (LC4)

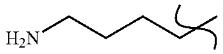

and R5 is H, then the corresponding residue consists of lysine (also termed "Lys").

In embodiments of a compound of formula (I) wherein A is group A1 and R3 is a group of formula (LC4)

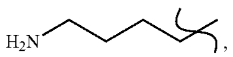

then the corresponding residue consists of lysine (also termed "Lys").

In embodiments of a compound of formula (I) wherein A is group A1 and R3 is a group of formula (LC5)

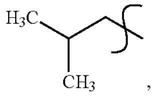

then the corresponding residue consists of leucine (also termed "Leu").

In embodiments of a compound of formula (I) wherein A is group A1 and R3 is a group of formula (LC6)

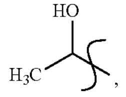

then the corresponding residue consists of threonine (also termed "Thr").

In embodiments of a compound of formula (I) wherein A is group A1 and R3 is a group of formula (LC7)

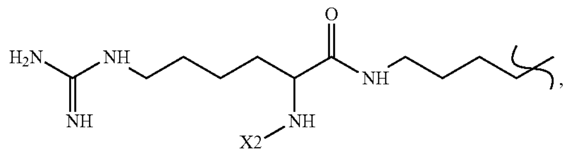

then the corresponding residue consists of Lys(X-hArg), X2 being selected in the group consisting of —H, —C(═O)—$CH_3$ and an amine protecting group Thus, the present disclosure encompasses two subfamilies of compounds, which may be termed (i) compounds (I-A1) for the compounds of formula (I) wherein group A is A1 and (ii) compounds (I-A2) for the compounds of formula (I) wherein group A is A2.

Compounds of formula (I-A1) are according to the below formula:

(I-A1)

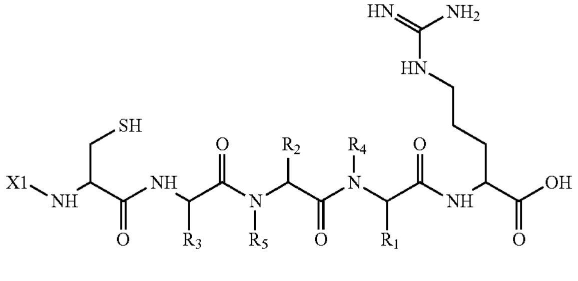

wherein R1, R2, R4, R5 are as defined for the general formula (I) and R3 and X1 are as defined for group A1.

Compounds of formula (I-A2) are according to the below formula:

(I-A2)

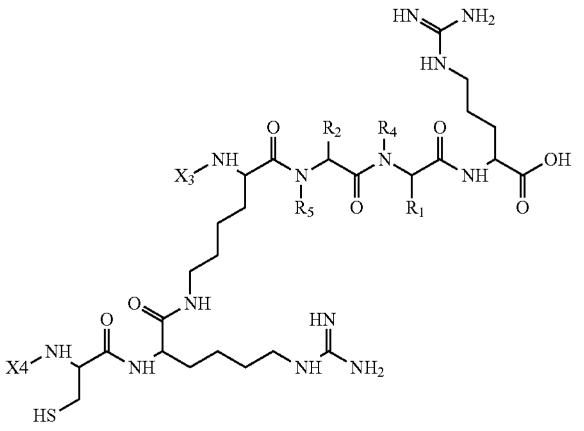

wherein R1, R2, R4, R5 and X1 are as defined for the general formula (I) and each of X3 and X4, identical or different, are selected in the group consisting of H, —C(═O)—CH3 and an amine protecting group.

As used herein, “Dap” means 2,3-diaminopropionic acid residue (or more accurately 2,3-diaminopropanoyl), “Dab” means 2,4-diaminobutyric acid residue (or more accurately 2,4-diaminobutanoyl), “ΔPro” means 3,4-dehydroproline residue (or more accurately 3,4-dehydroprolyl) and “Oic” means octahydro-1H-indole-2-carboxylic acid residue (or more accurately octahydro-1H-indole-2-carbonyl).

As used herein, “Pro” means proline (or more accurately prolyl), “Arg” means arginine (or more accurately an arginyl), “Lys” means lysine (or more accurately an lysyl), “Leu” means leucine (or more accurately a leucyl), “Thr” means threonine (or more accurately a threonyl) and “Lys (hArg)” means a lysine (homoarginine) moiety (or more accurately a Lysyl(homoArginyl), wherein the ε amine group of Lys forms amide bond with homoarginine (hArg) carboxyl group.

In some embodiments, an isomeric form of a compound of formula (I) consists of the compound (I') below:

(I')

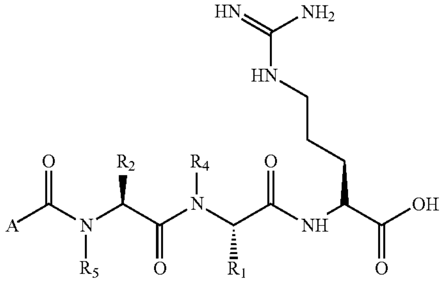

wherein R1, R2, R4, and R5 are as defined for the compound of formula (I),

A is selected in the group of formulas A1' and A2' below:

(A1')

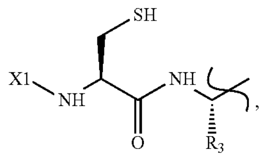

wherein R3 and X1 are as defined for the compound of formula (I), and (A2')

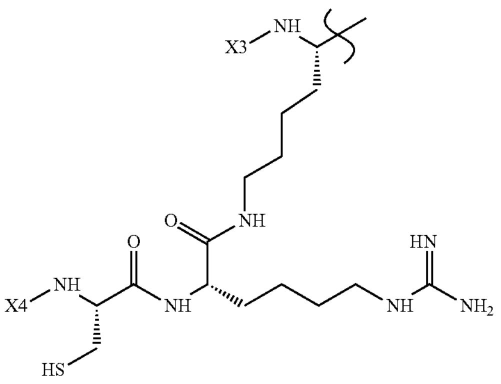

wherein each of X3 and X4, which are identical or different, are selected in the group consisting of H, —C(═O)—CH3 and an amine protecting group), and any pharmaceutically acceptable salts and/or racemic, enantiomeric, diastereoisomeric or tautomeric forms thereof.

The terms “protecting group” and “protecting groups” as used herein refer to any atom or group of atoms that is added to a molecule in order to prevent existing groups in the molecule from undergoing unwanted chemical reactions. A “protecting group” may be a labile chemical moiety that is known in the art to protect reactive groups, such as hydroxyl, amino and thiol groups, against undesired or untimely reactions during chemical synthesis. Protecting groups are typically used selectively and/or orthogonally to protect sites during reactions at other reactive sites and can then be removed to leave the unprotected group as is or available for further reactions.

Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art.

Amine protecting groups (which may also be termed amino protecting groups) encompass Fmoc (9-fluorenylmethyloxycarbonyl), Boc (tert-butyloxycarbonyl), Cbz (benzyloxycarbonyl), Ac (acetyl), Alloc (allyloxycarbonyl), Ts (p-toluenesulfonyl) groups. Protecting groups proposed for functional groups in the side chains of the residues (also termed "side chains protecting groups" herein) encompass e.g. 2,2,4,6,7-pentamethyldihydrobenzofurane-5-sulfonyl group (Pbf) and Boc for guanidine; tripheylmethyl group (Trt), p-methylbenzyl (Meb), acetamidomethyl (Acm) for thiol group.

As used herein, a compound of formula (I) encompasses a compound of formula (I'). Thus, an embodiment relating to compound (I) as described herein encompasses the same embodiment of the corresponding compound of formula (I').

As used herein, group A1 of a compound of formula (I) encompasses group A1'. Thus, an embodiment relating to group A1 of a compound (I) as described herein encompasses the corresponding embodiment of group A1'.

As used herein, group A2 of a compound of formula (I) encompasses group A2'. Thus, an embodiment relating to group A2 of a compound (I) as described herein encompasses the corresponding embodiment of group A2'.

As it is shown in the examples, the compounds of formula (I) as described herein possess high binding properties to NRP-1, and thus a high level ability to inhibit or block the interaction between NRP-1 and VEGF-$A_{165}$.

More precisely, the inventors have shown that the compounds of formula (I) disclosed herein bind to NRP-1 at the nanomolar level whereas the most efficient known inhibitors to date bind to NRP-1 at the micromolar level. As shown in the examples, the compounds of formula (I) bind to NRP-1 with an $IC_{50}$ value of equal or less than 100 nM, as determined by a chemiluminescence binding assay wherein the inhibition of the biding of VEGF-$A_{165}$ to immobilized NRP-1 by compounds of formula (I) was measured.

As used herein, the term "VEGF-$A_{165}$" (which is also termed "VEGFA165") is a human Vascular Endothelial Growth Factor isoform, which consists of a disulfide-linked homodimer containing two polypeptides chains of 165 amino acids each.

In most preferred embodiments, VEGF-$A_{165}$ is a homodimer polypeptide containing two identical polypeptide chains and having the NCBI reference number NP 001165097.

As used herein, "NRP-1" means Neuropilin-1, which is a protein belonging the Neuropilins family of cell surface receptors, which are engaged in multiple important cellular signalling cascades. NRP-1 is a co-receptor for tyrosine kinases (VEGF-R1, VEGF-R2, VEGF-R3) and its signalling is critical for VEGF-$A_{165}$/VEGF-R2 and VEGF-$A_{165}$/VEGF-R1-mediated angiogenesis, tumor growth and fundamental in the transition of tumours from a benign state to a malignant.

In most preferred embodiments, NRP-1 is the human polypeptide having 923 amino acids in length consisting of the sequence having the GenBank reference number AAC51759.1.

As it is apparent throughout the present disclosure, the compounds of formula (I), which includes compounds (I') as it is previously mentioned, all possess at least one common feature consisting of a sulfhydryl group which is borne by the cysteine residue located at the N-terminal side thereof.

Each compound of formula (I) comprises a cysteine residue located at the N-terminal side thereof. As it is shown in the examples herein, the cysteine residue comprised in a compound of formula (I) shall not be compulsory the N-terminal amino acid thereof. In some embodiments of a compound of formula (I), the cysteine residue is bound to the peptide backbone through the alpha amino group of homoarginine in lysine (homoarginine) moiety thereof.

Without wishing to be bound by any particular theory, the inventors believe that the presence of the cysteine residue in a compound of formula (I), which includes the presence of the sulfhydryl group thereof at the N-terminal side of a compound of formula (I), imparts the high binding level of a compound of formula (I) to NRP-1, and especially to human NRP-1.

Illustratively, in embodiments of a compound of formula (I) (and of formula (I')) wherein Group A is A1 (or A1'), a cysteine residue is the N-terminal amino acid thereof and is linked to the alpha amino group of an amino acid selected in the group consisting of lysine, leucine, threonine and lysine in lysine (homoarginine) moiety.

Still illustratively, in embodiments of a compound of formula (I) (and of formula (I')) wherein group A is A2 (or A2'), a cysteine residue is located at the N-terminal side thereof, and is linked to the alpha amino group of a homoarginine residue in N-terminal lysine (homoarginine) moiety.

Without wishing to be bound by any particular theory, the inventors believe that important moieties of a compound of formula (I) that impart a high level of binding to NRP-1, and thus a high level of anti-angiogenic activity, are (i) the presence of a cysteine residue at the N-terminal side and (ii) the presence of an arginine residue as the C-terminal amino acid.

Without wishing to be bound by any particular theory, the inventors believe that the presence of proline analogues instead of proline residues in a compound of formula (I) also contribute to optimization of the high capacity of a compound of formula (I) to bind to NRP-1. The replacement of proline residues by proline analogues has been already shown in the art to improve affinity of peptide-like ligands to NRP-1 (Puszko et al., 2019, MedChemComm, Vol. 10(2): 332-340).

A used herein, "proline analogues" consist of proline mimetics compounds differing from the proline residue by their rigidness as well as by their ring size. Most preferred embodiments of proline analogs in the present disclosure are selected in the group consisting of ΔPro, and Oic.

Proline under the form of the compound not linked to other residues is the compound of formula (B1) below:

(B1)

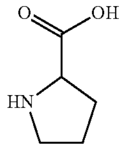

Proline, under the form of the compound linked to other residues, is the compound of formula (B2) below:

(B2)

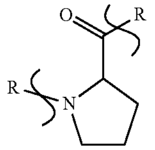

Proline analogue ΔPro, under the form of the compound not linked to other residues, is the compound of formula (C1) below:

(C1)

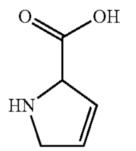

Proline analogue ΔPro, under the form of the compound linked to other residues, is the compound of formula (C2) below:

(C2)

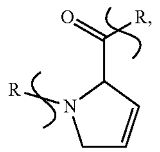

wherein R is a generic symbol for atoms to which ΔPro is bound in a compound in which ΔPro is comprised.

Proline analogue Oic, under the form of the compound not linked to other residues is the compound of formula (D1) below:

(D1)

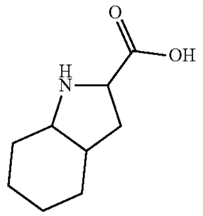

Proline analogue Oic, under the form of linked to other residues, is the compound of formula of formula (D2) below:

(D2)

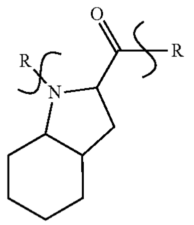

wherein R is a generic symbol for atoms to which Oic is bound in a compound in which Oic is comprised.

In some embodiments of a compound of formula (I) wherein group A is A1, R3 is a group of formula (LC7)

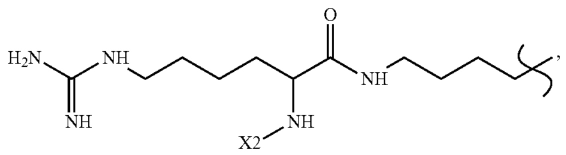

and, and R1, R2, R4, R5, X1, and X2 are as defined in the general definition of a compound of formula (I). In some of these embodiments, all of X1 and X2 are H. In these embodiments of R3, the side chain of lysine, wherein the ε amine group of Lys forms amide bond with homoarginine (hArg) carboxyl group. X1 and X2, identical or different, are selected in the group consisting of —H, —C(═O)—$CH_3$ and an amine protecting groups In some embodiments of a compound of formula (I) wherein group A is A1, R1 and R4, together with the carbon and nitrogen atoms to which they are linked, form a 2,5-dihydro-1-H-pyrrolyl ring, and R2, R3, R5, X1 and X2 are as defined in the general definition of a compound of formula (I). In some of these embodiments, X1 is H.

In some embodiments of a compound of formula (I) wherein group A is A1, R1 and R4, together with the carbon and nitrogen atoms to which they linked, form a octahydro-1H-indolyl ring, and R2, R3, R5, X1 and X2 are as defined in the general definition of a compound of formula (I). In some of these embodiments, X1 and X2 are both H.

In some embodiments of a compound of formula (I) wherein group A is A2, R1 and R4, together with the carbon and nitrogen atoms to which they linked, a 2,5-dihydro-1-H-pyrrolyl ring, and R2, R5 and X1, and X4 are as defined in the general definition of a compound of formula (I). In some of these embodiments, X1 and X4 are all H.

In some embodiments of a compound of formula (I) wherein group A is A2, R1 and R4, together with the carbon and nitrogen atoms to which they linked, a octahydr1H-indolyl ring, and R2, R5 and X1 and X4 are as defined in the general definition of a compound of formula (I). In some of these embodiments, X1 and X4 are all H.

In some embodiments of a compound of formula (I) wherein group A is A1, R2 is a group of formula (LC1)

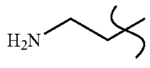

and R5 is H, and R1, R3, R4, X1 and X2 are as defined in the general definition of a compound of formula (I). In some of these embodiments, X1 is H.

In some embodiments of a compound of formula (I) wherein group A is A2, R2 is a group of formula (LC1)

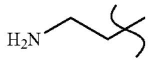

and R5 is H, and R1, R4 and X1 and X4 are as defined in the general definition of a compound of formula (I). In some of these embodiments, X1 and X4 are all H.

In some embodiments of a compound of formula (I) wherein group A is A1, R1 and R4, together with the carbon and nitrogen atoms to which they linked, form a 2,5-dihydro-1-H-pyrrolyl ring, R2 is a group of formula (LC1)

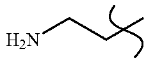

and R5 is H, R3 is a group of formula (LC7)

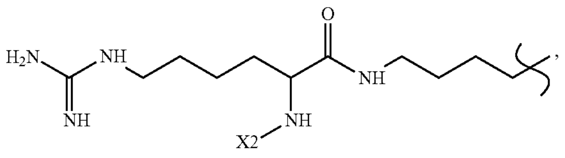

and X1, and X2 are as defined in the general definition of a compound of formula (I). In some of these embodiments, X1 and X2 are all H.

In some embodiments of a compound of formula (I) wherein group A is A1, R1 and R4, together with the carbon and nitrogen atoms to which they linked, form a octahydro-1H-indolyl ring, R2 is a group of formula (LC1)

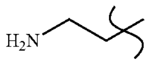

and R5 is H, R3 is a group of formula (LC7)

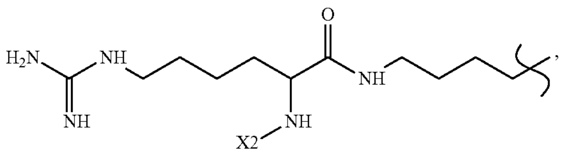

and X1 and X2 are as defined in the general definition of a compound of formula (I). In some of these embodiments, X1 and X2 are all H.

In some embodiments of a compound of formula (I) wherein group A is A2, R1 and R4, together with the carbon and nitrogen atoms to which they linked, a 2,5-dihydro-1-H pyrrolyl ring, R2 is a group of formula (LC1)

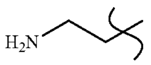

and R5 is H, and X1 and X4 are as defined in the general definition of a compound of formula (I). In some of these embodiments, X1 and X4 are all H.

In some embodiments of a compound of formula (I) wherein group A is A2, R1 and R4, together with the carbon and nitrogen atoms to which they linked, a octahydro-1H-indolyl ring, R2 is a group of formula (LC1)

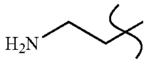

and R5 is H, and X1 and X4 are as defined in the general definition of a compound of formula (I). In some of these embodiments, X1 and X4 are all H.

In some embodiments of a compound of formula (I), the said compound consists of the compound of formula (I-A) below:

(I-A)

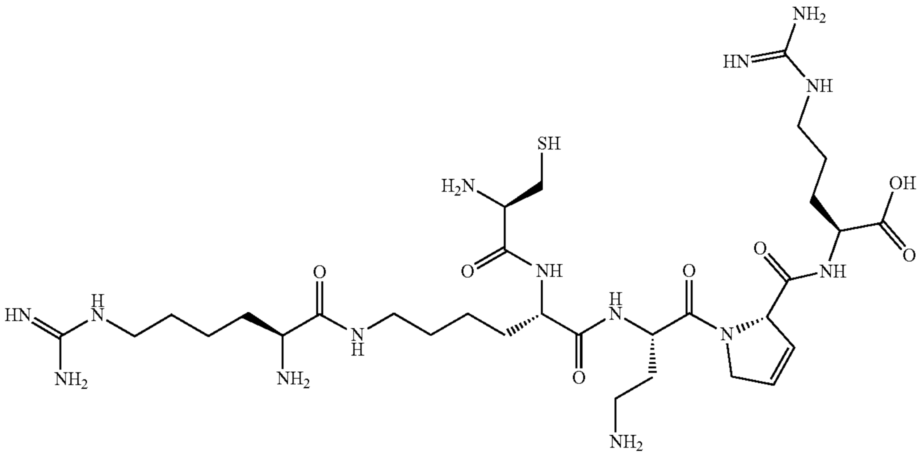

The compound of formula (I-A) may also be termed H-Cys-Lys(hArg)-Dab-ΔPro-Arg-OH herein.

In some embodiments of a compound of formula (I), the said compound consists of the compound of formula (I-B) below:

(I-B)

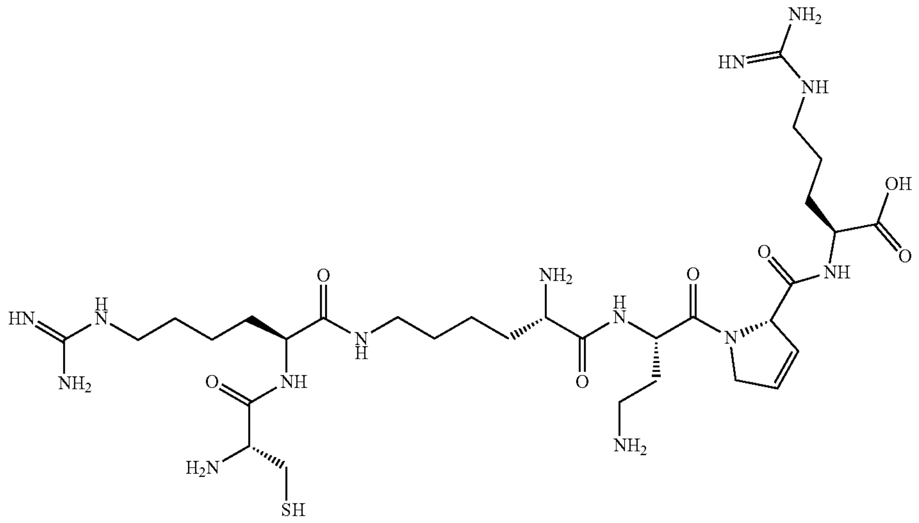

The compound of formula (I-B) may also be termed H-Lys(Cys-hArg)-Dab-ΔPro-Arg-OH herein.

In some embodiments of a compound of formula (I), the said compound consists of the compound of formula (I-C) below:

(I-C)

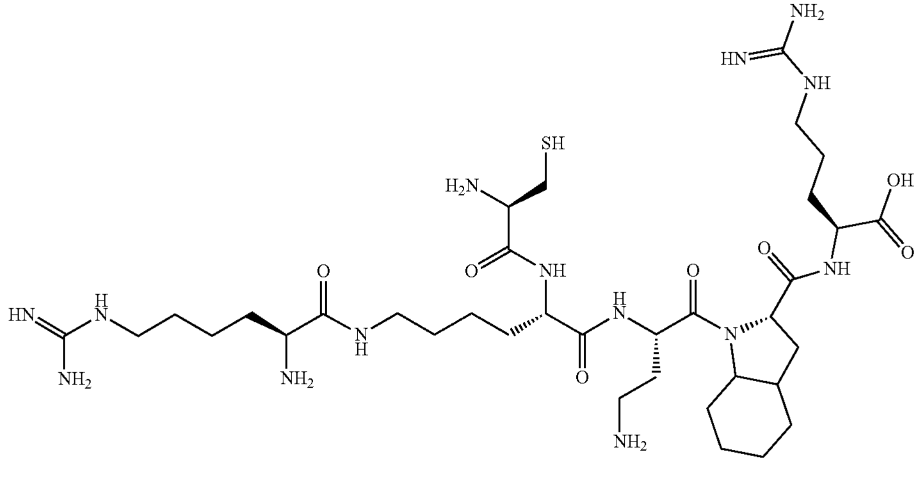

The compound of formula (I-C) may also be termed H-Cys-Lys(hArg)-Dab-Oic-Arg-OH herein.

In some embodiments of a compound of formula (I), the said compound consists of the compound of formula (I-D) below:

(I-D)

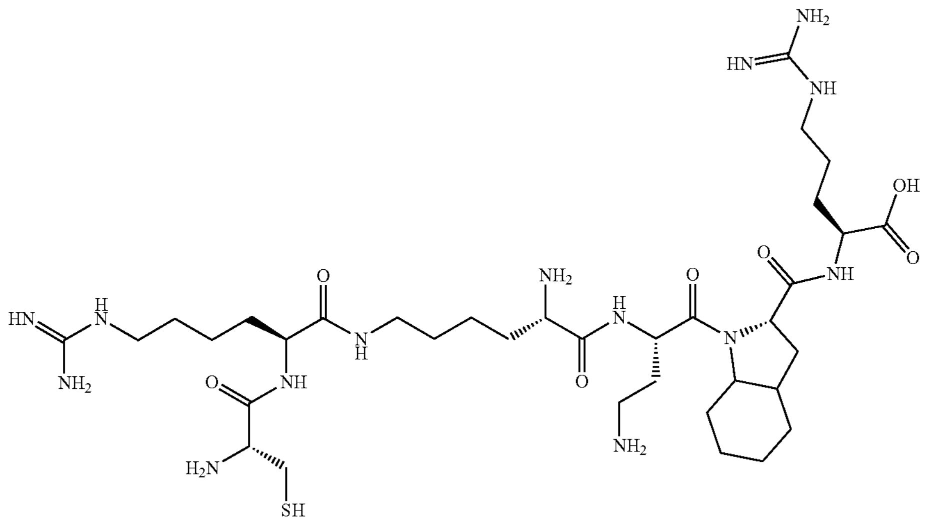

The compound of formula (I-D) may also be termed H-Lys(Cys-hArg)-Dab-Oic-Arg-OH herein.

The compounds of the invention may also exist in the form of bases or of acid-addition salts. These salts are pharmaceutically acceptable acids and also form part of the invention. In some embodiments, a compound of formula (I) is under the form of a trifluoroacetate salt.

The term "pharmaceutically acceptable" means what is useful in preparing a pharmaceutical composition generally safe, non-toxic, and neither biologically nor otherwise undesirable and includes what is acceptable for veterinary as well as human pharmaceutical use.

In addition to pharmaceutically-acceptable salts, other salts are included in the invention. They may serve as intermediates in the purification of the compounds, in the preparation of other salts, or in the identification and characterization of the compounds or intermediates.

The compounds of the invention may also exist in the form of hydrates or solvates, i.e. in the form of associations or combinations with one or more molecules of water or with a solvent such as methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present disclosure.

The present disclosure also encompasses one of the pharmaceutically acceptable salts and/or racemic, enantiomeric, diastereoisomeric or tautomeric forms of any of the compounds of formula (I) specified in the present disclosure.

Methods for Preparing Compounds of Formula (I)

Methods for preparing compounds of formula (I) are disclosed in detail in the examples. These methods are illustrated hereunder for preparing compounds of formula (I').

First Preparation Method

The present disclosure relates to a method for preparing a compound of formula (I), wherein group A consists of group (A1)

(I')

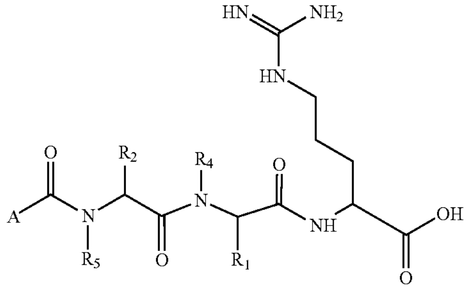

wherein, for groups R1 and R4, a) R1 is a group of formula (LC1)

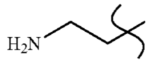

and R4 is H, or b) R1 and R4, together with the carbon and nitrogen atoms to which they are linked, form a pyrrolidinyl ring, or c) R1 and R4, together with the carbon and nitrogen atoms to which they are linked, form a 2,5-dihydro-1-H-pyrrolyl ring, or d) R1 and R4, together with the carbon and nitrogen atoms to which they are linked, form a octahydro-1H-indolyl ring, or e) R1 is a group of formula (LC2)

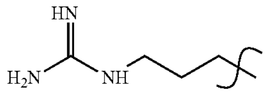

and R4 is H.

for groups R2 and R5, a) R2 is a group of formula (LC3)

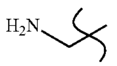

and R5 is H, or b) R2 is a group of formula (LC1)

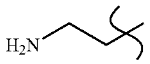

and R5 is H, or c) R1 and R4, together with the carbon and nitrogen atoms to which they are linked, form a pyrrolidinyl ring, or d) R2 and R5, together with the carbon and nitrogen atoms to which they are linked, form a 2,5-dihydro-1-H-pyrrolyl ring, or e) R2 and R5, together with the carbon and nitrogen atoms to which they are linked, form a octahydro-1H-indolyl ring, or f) R2 is a group of formula (LC2)

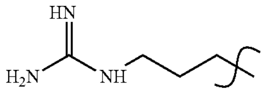

and R5 is H, or g) R2 is a group of formula (LC3)

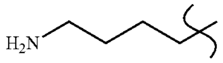

and R5 is H, . . .

A is of formula A1' below:

(A1')

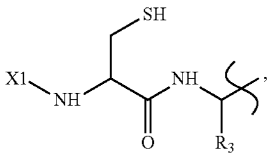

wherein X1 is selected in the group consisting of H, —C(═O)—CH3 and an amine protecting group, and wherein R3 is selected in the group consisting of a) R3 is a group of formula (LC3)

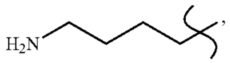

or b) R3 is a group of formula (LC4)

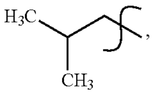

or c) R3 is a group of formula (LC5)

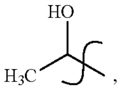

or d) R3 is a group of formula (LC7)

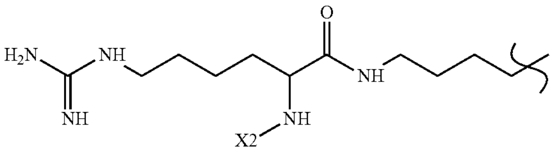

and wherein X2 is selected in the group consisting of H, —C(═O)—CH3 and an amine protecting group.

The present disclosure relates to a method for preparing a compound of formula (I), wherein group A consists of group (A1), R3 is Lys(hArg) moiety and comprising the steps of:

a) alpha amine group deprotection and reaction of a compound of formula (II-1') below (II-1')

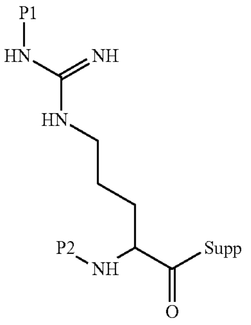

wherein P1 means a guanidine protecting group and P2 means an alpha-amine protecting group, P1 and P2 being most preferably distinct and "Supp" means a solid support, with an alpha-amine protected amino acid (for secondary amine groups) or an alpha amine and side chain protected amino acid (for primary amines), so as to obtain a compound of formula (II-2') below (II-2')

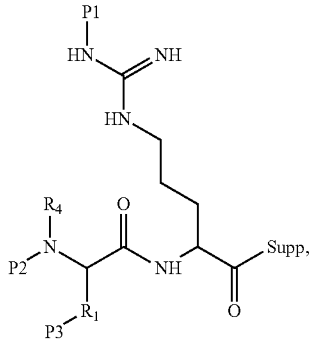

wherein Supp means a solid support, P1 means a guanidine protecting group, P2 means an amine protecting group, P3 means a side chain protecting group and R1 and R4 are as defined for the compound of formula (I), b) alpha amine group deprotection and reaction of a compound of formula (II-2') with an alpha amine protected amino acid (for secondary amines) or an alpha amine and side chain protected amino acid (for primary amines), so as to obtain a compound of formula (II-3') below (II-3')

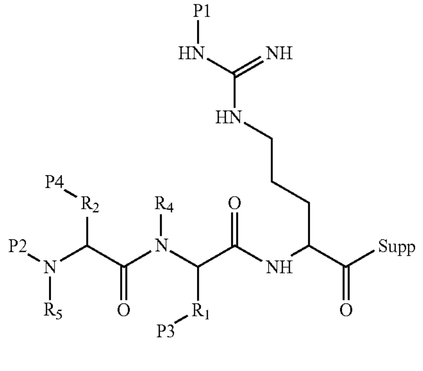

wherein Supp means a solid support, P1 means a guanidine protecting group, P2 means an alpha amine protecting group, each of P3 and P4, identical or different, mean a side chain protecting groups and R1, R2, R4 and R5 are as defined for the compound of formula (I), c) alpha amine group deprotection and reaction of the compound of formula (II-3') obtained at step b) with a protected lysine amino acid, so as to obtain a compound of formula (II-4') below (II-4')

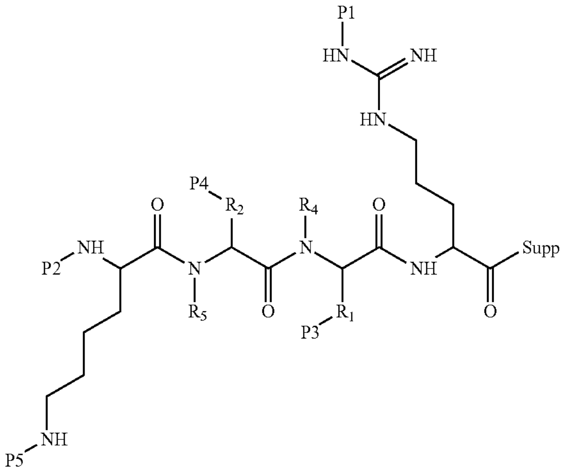

wherein Supp means a solid support, P1 means a guanidine protecting group, P2 means an alpha amine protecting group, each of P3 and P4, identical or different, mean a side chain protecting groups, P5 means orthogonal amine protecting group, P1, P2, P3, P4 and P5 being most preferably distinct, and R1, R2, R4 and R5 are as defined for the compound of formula (I), d) alpha amine group deprotection and reaction of a compound of formula (II-4') obtained at step c) with a protected cysteine amino acid, so as to obtain a compound of formula (II-5') below (II-5')

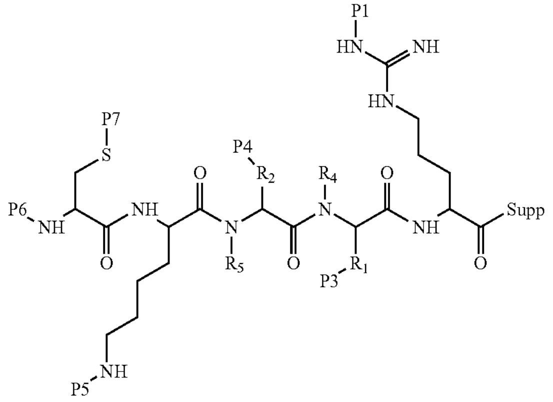

wherein Supp means a solid support, P1 means a guanidine protecting group, P3 and P4 mean a side chain protecting groups, P5 and P6 mean amine protecting groups, P7 means a thiol protecting group and R1, R2, R4 and R5 are as defined for the compound of formula (I), e) epsilon amine group deprotection and reaction of a compound of formula (II-5') obtained at step d) with a protected hArg amino acid, so as to obtain a compound of formula (II-6') below (II-6')

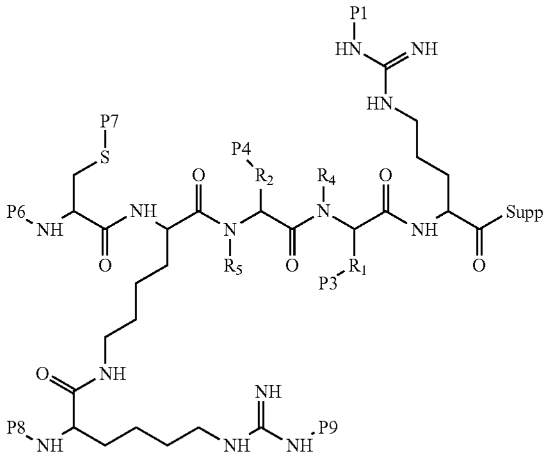

wherein Supp means a solid support, P1 and P9 mean guanidine protecting groups, each of P3 and P4 mean a side chain protecting groups, P6 and P8 mean amine protecting groups, P7 means a thiol protecting group, P1, P3, P4, P6, P7, P8 and P9 being distinct, and R1, R2, R3, R4 and R5 are as defined for the compound of formula (I), and f) removing the compound of formula (II-6') from the solid support and removing side chains and/or alpha amine protecting groups so as to obtain the said compound of formula (I).

At step a), the compound of formula (II-1') is immobilized on a solid support (termed "Supp") which may be any solid support for solid synthesis methods that are known from the one skilled in the art. The solid support is preferably a resin support for solid synthesis methods which is well known form the skilled artisan, such as a Wang resin commercialized by Activotec (Cambridge, United Kingdom). Wang resin is notably disclosed in Wang, S. S., 1973, J. Am Chem Soc, Vol. 95: 1328).

In some embodiments, the purified compound of formula (I) is lyophilized.

Second Preparation Method

The present disclosure relates to a method for preparing a compound of formula (I), wherein group A consists of group (A2).

(I)

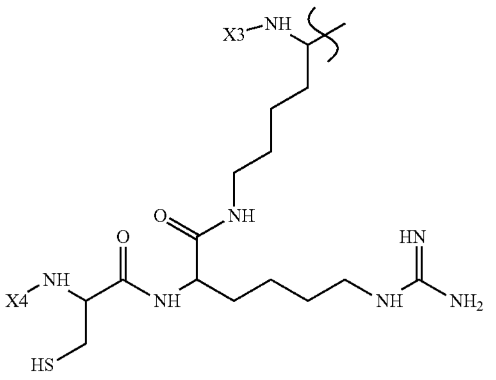

wherein X3 and X4, which are identical or different, are selected in the group consisting of H, —C(═O)—CH3 and an amine protecting group and wherein, for groups R1 and R4, a) R1 is a group of formula (LC1)

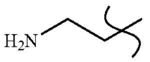

and R4 is H, or b) R1 and R4, together with the carbon and nitrogen atoms to which they are linked, form a pyrrolidinyl, or c) R1 and R4, together with the carbon and nitrogen atoms to which they are linked, form a 2,5-dihydro-1-H-pyrrolyl, or d) R1 and R4, together with the carbon and nitrogen atoms to which they are linked, form a octahydro-1H-indolyl, or e) R1 is a group of formula (LC2)

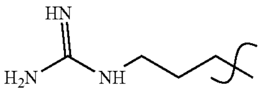

and R4 is H.

for groups R2 and R5, a) R2 is a group of formula (LC3)

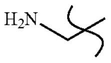

and R5 is H H, or b) R2 is a group of formula (LC1)

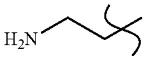

and R5 is H, or c) R1 and R4, together with the carbon and nitrogen atoms to which they are linked, form a pyrrolidinyl, or d) R2 and R5, together with the carbon and nitrogen atoms to which they are linked, form a 2,5-dihydro-1-H pyrrolyl, or e) R2 and R5, together with the carbon and nitrogen atoms to which they are linked, form a octahydro-1H-indolyl, or f) R2 is a group of formula (LC2)

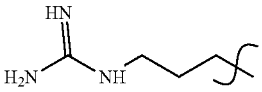

and R5 is H, or g) R2 is a group of formula (LC3)

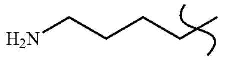

and R5 is H.

A is the group of formula A2 below:

(A2')

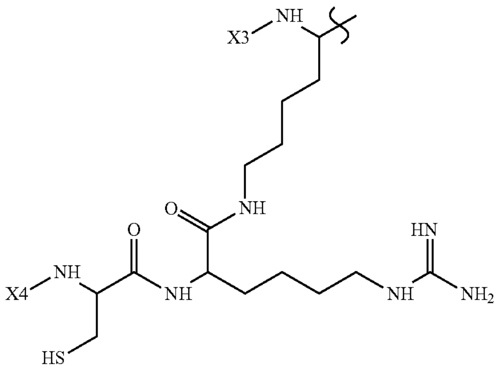

wherein X3 and X4, which are identical or different, are selected in the group consisting of H, —C(═O)—CH3 and an amine protecting group), comprising the steps of:

a) alpha amine group deprotection and reaction of a compound of formula (II-1') below (II-1')

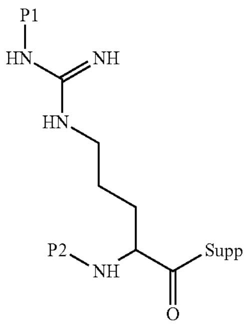

wherein P1 means a guanidine protecting group and P2 means an alpha-amine protecting group, P1 and P2 being most preferably distinct and "Supp" means a solid support, with an alpha-amine protected amino acid (for secondary amine groups) or an alpha amine and side chain protected amino acid (for primary amines), so as to obtain a compound of formula (II-2') below (II-2')

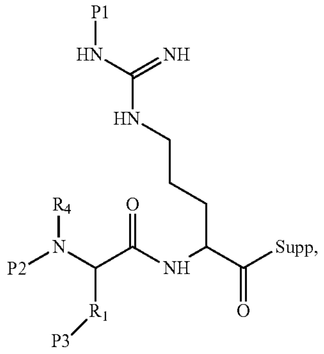

wherein Supp means a solid support, P1 means a guanidine protecting group, P2 means an amine protecting group, P3 means a side chain protecting group and R1 and R4 are as defined for the compound of formula (I), b) alpha amine group deprotection and reaction of a compound of formula (II-2') with an alpha amine protected amino acid (for secondary amines) or an alpha amine and side chain protected amino acid (for primary amines), so as to obtain a compound of formula (II-3') below (II-3')

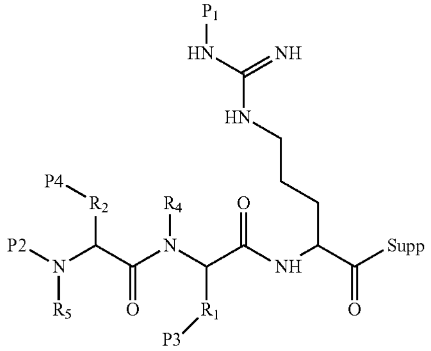

wherein Supp means a solid support, P1 means a guanidine protecting group, P2 means an alpha amine protecting group, each of P3 and P4, identical or different, mean a side chain protecting groups and R1, R2, R4 and R5 are as defined for the compound of formula (I), c) alpha amine group deprotection and reaction of the compound of formula (II-3') obtained at step b) with a protected Lysine amino acid, so as to obtain a compound of formula (II-6') below (II-6')

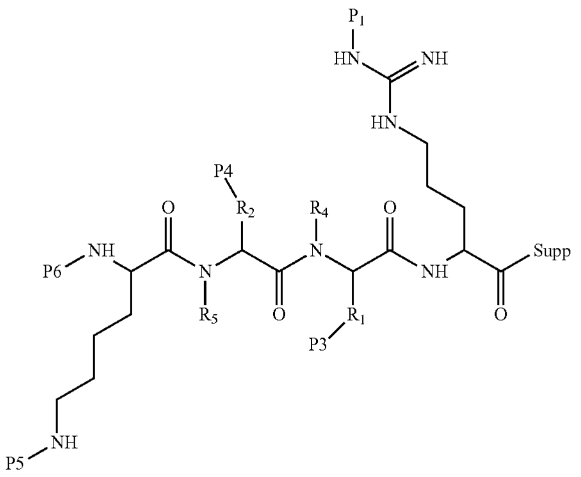

wherein Supp means a solid support, P1 means a guanidine protecting group, each of P3 and P4, identical or different, mean a side chain protecting groups, P5 and P6 means orthogonal amine protecting group, P1, P3, P4, P5 and P6 being most preferably distinct, and R1, R2, R4 and R5 are as defined for the compound of formula (I), d) epsilon amine group deprotection and reaction of a compound of formula (II-6') obtained at step c) with a protected homoarginine (hArg) amino acid so as to obtain a compound of formula (II-7') below (II-7')

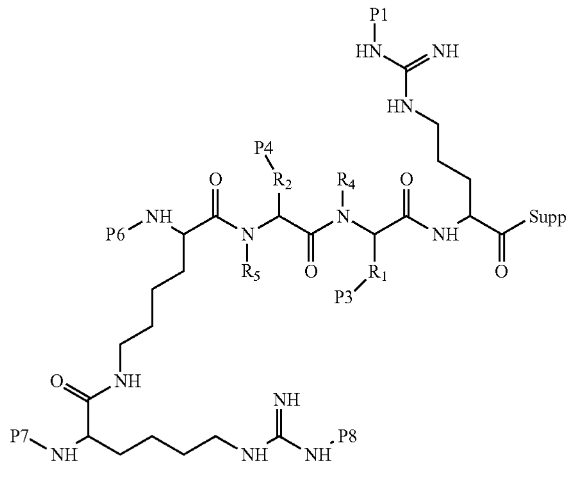

wherein Supp means a solid support, P1 and P8 mean a guanidine protecting groups, each of P3 and P4, identical or different, mean a side chain protecting groups, P6 and P7 mean orthogonal amine protecting group, P1, P2, P3, P4 and P5 being most preferably distinct, and R1, R2, R4 and R5 are as defined for the compound of formula (I)

e) amine group deprotection and reaction of a compound of formula (II-7') obtained at step d) with a protected cysteine amino acid, so as to obtain a compound of formula (II-8') below (II-8')

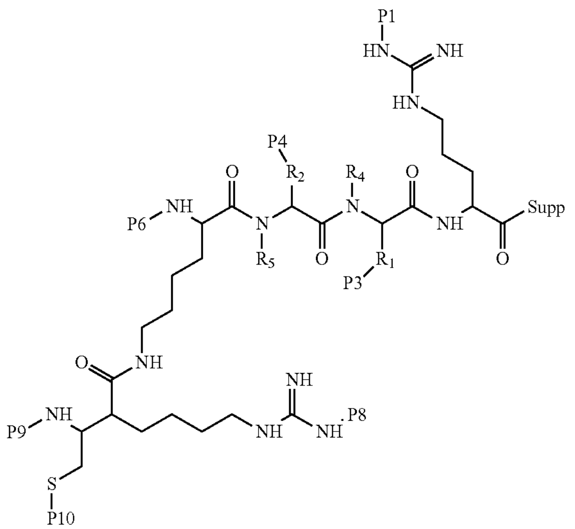

wherein Supp means a solid support, P1 and P8 mean a guanidine protecting groups, each of P3 and P4, identical or different, mean a side chain protecting groups, P6 and P9 mean amine protecting groups, P10 means thiol protecting group, P1, P2, P3, P4 and P5 being most preferably distinct, and R1, R2, R4 and R5 are as defined for the compound of formula (I), and f) removing the compound of formula (II-8') from the solid support and removing side chains and/or alpha amine protecting groups so as to obtain the said compound of formula (I).

In some embodiments, the purified compound of formula (I) is lyophilized.

Pharmaceutical Compositions

The present disclosure further relates to a pharmaceutical composition comprising a compound of formula (I) as disclosed herein, optionally in combination with one or more pharmaceutically compatible excipients.

As already specified in the present disclosure, compounds of formula (I) encompass the corresponding compounds of formula (I') disclosed herein.

As it shall be readily understood from the present disclosure, compounds of formula (I) that may be used for prophylactic or therapeutic purpose, and thus be comprised in a pharmaceutical composition, are those that are devoid of any protecting group, i.e. any compound of formula (I) disclosed herein for which group X is H.

In some embodiments, the composition (e.g., pharmaceutical composition) further comprises a pharmaceutically acceptable carrier. In some embodiments, the composition (e.g., pharmaceutical composition) is useful for treating a disease or disorder associated with angiogenesis, especially a disease or disorder associated with $VEGF-A_{165}$/NRP-1 interaction, and most preferably a cancer.

Compositions (e.g., pharmaceutical compositions) of the present disclosure are formulated based upon the mode of delivery, including, for example, compositions formulated for delivery to the liver via parenteral delivery.

The compositions (e.g., pharmaceutical composition) of the present disclosure may be administered in dosages sufficient to inhibit $VEGF-A_{165}$/NRP-1 interaction. In some embodiments, a suitable dose of a compound of formula (I) is in the range of 0.001 mg/kg-1000 mg/kg body weight of the recipient.

One of ordinary skill in the art will appreciate that certain factors may influence the dosage and timing required to effectively treat a subject, including, but not limited to, severity of the disease or disorder, previous treatments, the general health and/or age of the subject, and one or more other diseases being present. Moreover, treatment of a subject with a therapeutically effective amount of a pharmaceutical composition can include a single treatment or a series of treatments.

Any compound selected in the group comprising compounds of formula (I) of the present disclosure can be formulated in a pharmaceutically acceptable carrier or diluent. Pharmaceutically acceptable carriers can be liquid or solid and may be selected with the planned manner of administration in mind so as to provide for the desired bulk, consistency, and other pertinent transport and chemical properties. Any known pharmaceutically acceptable carrier or diluent may be used, including, for example, water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), calcium salts (e.g., calcium sulfate, calcium chloride, calcium phosphate, etc.) and wetting agents (e.g., sodium lauryl sulfate).

Any compound of formula (I) of the present disclosure can be formulated into compositions (e.g., pharmaceutical compositions) containing the said active compound admixed, encapsulated, conjugated, or otherwise associated with other molecules, molecular structures, or mixtures of nucleic acids.

As used herein the expression "compound selected in the group comprising" encompasses "compound selected in the group consisting of".

Therapeutic Uses

The present disclosure provides a compound of formula (I) as disclosed herein, or one of its pharmaceutically acceptable salts and/or racemic, enantiomeric, diastereoisomeric or tautomeric forms, for its use as a medicament. It relates to the use of a compound of formula (I) as disclosed herein, or one of its pharmaceutically acceptable salts and/or racemic, enantiomeric, diastereoisomeric or tautomeric forms, for preparing a medicament.

The present disclosure also pertains to a compound of formula (I) as disclosed herein, or one of its pharmaceutically acceptable salts and/or racemic, enantiomeric, diastereoisomeric or tautomeric forms, for its use for preventing or treating a disease involving a VEGF-$A_{165}$/NRP-1 interaction. It relates to the use of a compound of formula (I) as disclosed herein, or one of its pharmaceutically acceptable salts and/or racemic, enantiomeric, diastereoisomeric or tautomeric forms, for preparing a medicament for preventing or treating a disease involving a $VEGF_{165}$/NRP-1 interaction.

The present disclosure further concerns a compound of formula (I) as disclosed herein, or one of its pharmaceutically acceptable salts and/or racemic, enantiomeric, diastereoisomeric or tautomeric forms, for its use for preventing or treating angiogenesis mediated by a VEGF-$A_{165}$/NRP-1 interaction in a diseased subject in need thereof. It relates to the use of a compound of formula (I) as disclosed herein, or one of its pharmaceutically acceptable salts and/or racemic, enantiomeric, diastereoisomeric or tautomeric forms, for preparing a medicament for preventing or treating angiogenesis mediated by a VEGF-$A_{165}$/NRP-1 interaction in a diseased subject in need thereof.

The present invention is related to the use of a compound of formula (I) for the preparation of a pharmaceutical composition or some pharmaceutical composition containing them targeting NRP-1 intended for the treatment of several disorders such as angiogenesis, cancer, diabetes, age-related macula degeneracy (AMD), rheumatoid Polyarthritis, immune diseases The present disclosure yet further relates to a compound of formula (I) as disclosed herein, or one of its pharmaceutically acceptable salts and/or racemic, enantiomeric, diastereoisomeric or tautomeric forms, for preventing or treating a cancer. It relates to the use of a compound of formula (I) as disclosed herein, or one of its pharmaceutically acceptable salts and/or racemic, enantiomeric, diastereoisomeric or tautomeric forms, for preparing a medicament for preventing or treating a cancer.

As used herein, the term "subject" relates to a human or non-human animal such as a mammal, which includes a rodent, a feline, a canine and a primate. Particularly, the subject according to the present disclosure is a human.

As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma;

glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Methods

The present disclosure also pertains to a prophylactic or therapeutic method for inhibiting VEGF-$A_{165}$/NRP-1 interaction in a subject in need thereof, comprising a step of administering to the said subject a compound of formula (I) disclosed herein, or one of its pharmaceutically acceptable salts and/or racemic, enantiomeric, diastereoisomeric or tautomeric forms.

The present disclosure relates to a method for preventing or treating a disease involving a VEGF-$A_{165}$/NRP-1 interaction comprising a step of administering to the said subject a compound of formula (I) disclosed herein, or one of its pharmaceutically acceptable salts and/or racemic, enantiomeric, diastereoisomeric or tautomeric forms.

The present disclosure further pertains to a method for preventing or treating angiogenesis mediated by a VEGF-$A_{165}$/NRP-1 interaction in a diseased subject, comprising a step of administering to the said subject a compound of formula (I) disclosed herein, or one of its pharmaceutically acceptable salts and/or racemic, enantiomeric, diastereoisomeric or tautomeric forms.

The present disclosure also concerns a method for preventing or treating a cancer in a subject in need thereof, comprising a step of administering to the said subject a compound of formula (I) disclosed herein, or one of its pharmaceutically acceptable salts and/or racemic, enantiomeric, diastereoisomeric or tautomeric forms.

The types of cancers that may be prevented of treated with a compound of formula (I), or one of its pharmaceutically acceptable salts and/or racemic, enantiomeric, diastereoisomeric or tautomeric forms, are specified elsewhere in the present description.

The medical method comprising administering a compound of formula (I), or one of its pharmaceutically acceptable salts and/or racemic, enantiomeric, diastereoisomeric or tautomeric forms, may be either "prophylactic" or "therapeutic". When provided prophylactically, the compound of formula (I) of the present disclosure is provided in advance of any symptom of a disease or condition. The prophylactic administration of the compound serves to prevent or ameliorate or delay time to onset of any subsequent disease. When provided therapeutically, the compound of formula (I) is provided at or after the onset of a symptom of disease.

The above prophylactic or therapeutic method encompasses administering to the said subject any of the embodiments of a compound of formula (I) disclosed herein, which encompasses compounds (I-A), (I-B) and (I-C) disclosed herein, or one of their pharmaceutically acceptable salts and/or racemic, enantiomeric, diastereoisomeric or tautomeric forms.

A compound of formula (I) used according to the invention may be administered in an effective dose by any of the accepted modes of administration in the art.

In one embodiment, this compound may be used in a composition intended to be administrated by oral, rectal or parenteral injection route, preferably by oral route, in particular diluted in a drink such as water.

The term "parenteral injection" refers to an administration via injection under or through one or more layers of skin or mucus membranes of a subject. This injection may be for instance intradermal, subcutaneous, intravenous or intramuscular.

According to another embodiment, the pharmaceutical composition of the invention is administered topically. Topical administration may be particularly advantageous for the treatment of skin cancers. Examples of formulations adapted to topical administration include, but are not limited to, patch, such as, for example, transdermic patch, ointment, gel, cream and the like.

According to another embodiment, for the treatment of conditions of the lungs or of the respiratory tract, aerosol delivery can be used.

Other examples of administration routes include, but are not limited to, nasal, buccal, rectal, vaginal, intratracheal, endoscopic and percutaneous administration.

According to an embodiment, the pharmaceutical composition of the invention is administered preoperatively, and/or postoperatively.

According to an embodiment, the method of the invention comprises the injection of the pharmaceutical composition of the invention, preferably the systemic injection. Examples of systemic injections include, but are not limited to, intravenous, subcutaneous, intramuscular, intradermal and intraperitoneal injection, and perfusion. According to another embodiment, the composition of the invention is intratumorally or intralesionally injected.

The route of administration and the galenic formulation will be adapted by one skilled in the art pursuant to the desired pharmaceutical effect.

According to an embodiment, the pharmaceutical composition of the invention is injected, preferably systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal and intraperitoneal injection, and perfusion.

According to an embodiment, when injected, the pharmaceutical composition of the invention is sterile. Methods for obtaining a sterile pharmaceutical composition include, but are not limited to, GMP synthesis (GMP stands for "Good manufacturing practice").

One of ordinary skill in the art of therapeutic formulations will be able, without undue experimentation and in reliance upon personal knowledge, to ascertain a therapeutically effective dose of a compound of the invention for a given indication.

The compound of the invention may be administered to a subject once a week, twice a week, four times a week, once a day, twice a day, three times a day or more if necessary, and such administration can be for one day, two days, three days, four days, five days, or a week, two weeks, three weeks, a month, or more than one month when required.

The present disclosure is further illustrated by the following examples.

EXAMPLES

Example

Example 1: Synthesis of the Peptide VEGF-A165/NRP-1 Inhibitors

Example 1 describes the general procedure for the synthesis of the compounds of formula (I).

Peptidomimetics of the present invention may be obtained by using the well-known procedures of the Solid Phase Peptide Synthesis (SPPS). The functional groups of the side-chains of the building blocks should be protected with orthogonal protecting groups (P) that are eliminated under acidic or basic conditions. The preferred N-α-protecting groups are: 9-fluorenylmethyloxycarbonyl group (Fmoc) or tert-butyloxycarbonyl group (Boc) for N-terminal amino acid for the synthesis of compounds of formula (I-A2). Other protecting groups preferred for the protection of functional groups in the side chain building blocks are: 2,2,4,6,7-pentamethyldihydrobenzofurane-5-sulfonyl group (Pbf), Boc, Fmoc, allyloxycarbonyl group (Alloc), triphey-lmethyl group (Trt). For the synthesis of peptidomimetics, C-terminal amino acid may be already attached to a polymeric support which is chemically inert and insoluble in the reaction media used. Wang resin is a preferred resin for the peptide synthesis in the Fmoc strategy. Peptide bonds can be obtained by using the standard coupling reagents: 1-[bis(dimethylamino)methylene]-1H-1,2,3-triazolo[4,5-b]pyridinium 3-oxid hexafluorophosphate (HATU) or O-(1H-6-chlorobenzotriazole-1-yl)-1,1,3,3-tetramethyluronium hexafluorophosphate (HCTU) in the presence of a base used for deprotonation of carboxylic acid, preferably N,N-diisopropylethylamine (DIPEA).

The final step of the synthesis, is the cleavage of the peptide from the resin and it is preferred to use a mixture of trifluoroacetic acid (TFA)/1,4-dithiothreitol (DTT)/water/triisopropylsilane (TIS) (88:5:5:2 v/w/v/v). The crude products may be purified using high performance liquid chromatography on a reverse phase column packed with a C-12 gradient of 0%-20% (B) over 30 minutes, where phase (A) is 0.1% TFA in $H_2O$ and the phase (B) is 0.1% TFA in acetonitrile (ACN). The products obtained can optionally be converted to a desired pharmaceutically acceptable salt using a conventional method.

B. Solid Phase Synthesis of Peptides of Formula (I)

The procedure for the synthesis of this group of compounds of the present invention is discussed below.

Example 2: Solid Phase Synthesis of the Compound of Formula (I) H-Cys-Lys(hArg)-Dab-ΔPro-Arg-OH, Wherein Group a is Group A1

In compound formulas illustrated in example 2, each of R1, R2, R3, R4 and R5, when present, have the same meanings as for the general definition of the compound of formula (I) specified in the present disclosure.

500 mg of pre-loaded Fmoc-L-Arg(Pbf) Wang resin with capacity 0.39 mmol/g was mixed in 6 ml of the N,N-dimethylformamide (DMF) for four hours.

Scheme 1

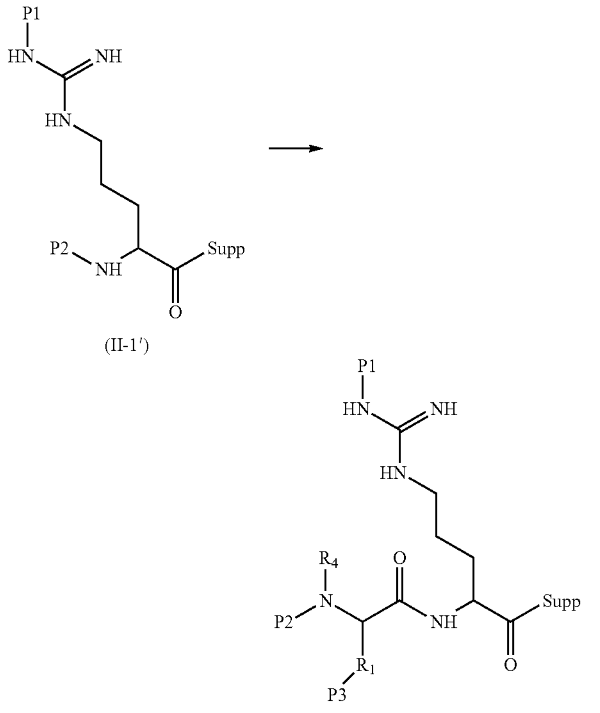

(II-1')

(II-2')

("Supp" means a solid support)

After that time, Fmoc-deprotection step was done: the resin was filtered off and then mixed in 6 ml of 20% (v/v) piperidine in DMF for 5 minutes, then the resin was filtered off and a fresh aliquot of 20% piperidine in DMF was added (6 ml) and stirred for another 20 minutes. Next, washing after Fmoc-deprotection step was done: the resin was washed alternately with 6 mL of DMF and 6 ml of isopropanol (IPA) three times for one minute each, followed by washing of the resin three times (for one minute) with a fresh portion of DMF. After the washing, for monitoring of the completion of the Fmoc cleavage, the colorimetric assay was made. Usually, for primary amines, this is the Kaiser test. For this purpose a few resin beads were placed in small test tube and few drops (equal volumes) of the three solutions [(A): 5 g of ninhydrin in 100 ml ethanol; (B): 80 g phenol in 20 ml of ethanol; (C) 2 ml 0.001 M aqueous KCN in 98 ml pyridine] were added. The test tube was placed in thermo block and heated for 5 minutes at 100° C. A positive Kaiser test result (deep blue colour of resin and solution) was obtained which allowed us to proceed to the next step wherein 2 eq of Fmoc-ΔPro-OH (134 mg; 0.4 mmol), 2 eq of HATU (152 mg; 0.2 mmol) and 5 eq of DIPEA (169 μL; 1 mmol) were dissolved in 5 ml of DMF—to form the preactivation mixture. The preactivation mixture was stirred for 1 minute and added to the resin and mixed for two hours. After this time the resin was filtered off and washed four times (1 minute) with DMF (6 ml) and then the colorimetric assay was made. For secondary amines, this is the acetaldehyde/chloranil test. For this purpose a few resin beads were placed in small test tube and few drops (equal volumes) of the two solutions [(A): 2% of chloranil in DMF; (B): 2% of acetaldehyde in DMF] were added. After a short mixing the mixture was left at room temperature for 5 minutes. A negative test result (which means the completion of the coupling reaction) was obtained which allowed us to proceed to the next step. Next, Fmoc-deprotection and washing after Fmoc-deprotection steps were done. After the wash sequence, for monitoring of the completion of the Fmoc cleavage, the acetaldehyde/chloranil test was made. The positive result of test was obtained (the dark blue colour of beads of resin indicated the completion of the Fmoc cleavage) which allowed to proceed to the coupling step.

Scheme 2

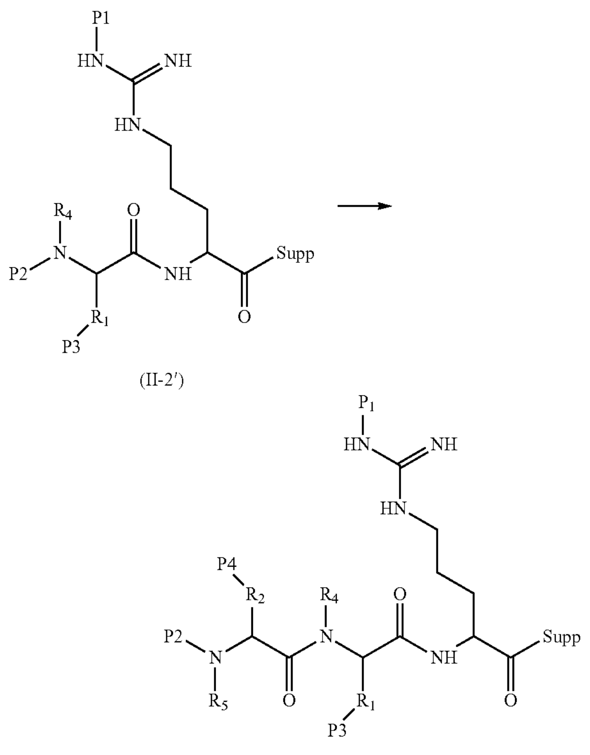

(II-2')

(II-3')

2 eq of Fmoc-Dab(Boc)-OH (176 mg; 0.4 mmol), 2 eq of HATU (152 mg; 0.2 mmol) and 5 eq of DIPEA (169 μL; 1 mmol) were dissolved in 5 ml of DMF. After 1 minute the preactivation mixture was added to the resin and mixed for two hours. After this time, the resin was filtered off and washed four times (1 minute) with a fresh portion (6 ml) of DMF, and then the Kaiser test was performed. The result of Kaiser test was negative, which means the completion of the coupling reaction. Next, Fmoc-deprotection and washing after Fmoc-deprotection steps were done. For monitoring of the completion of the Fmoc cleavage the Kaiser test was performed. Negative result of the test allowed us to proceed to the coupling step.

Scheme 3

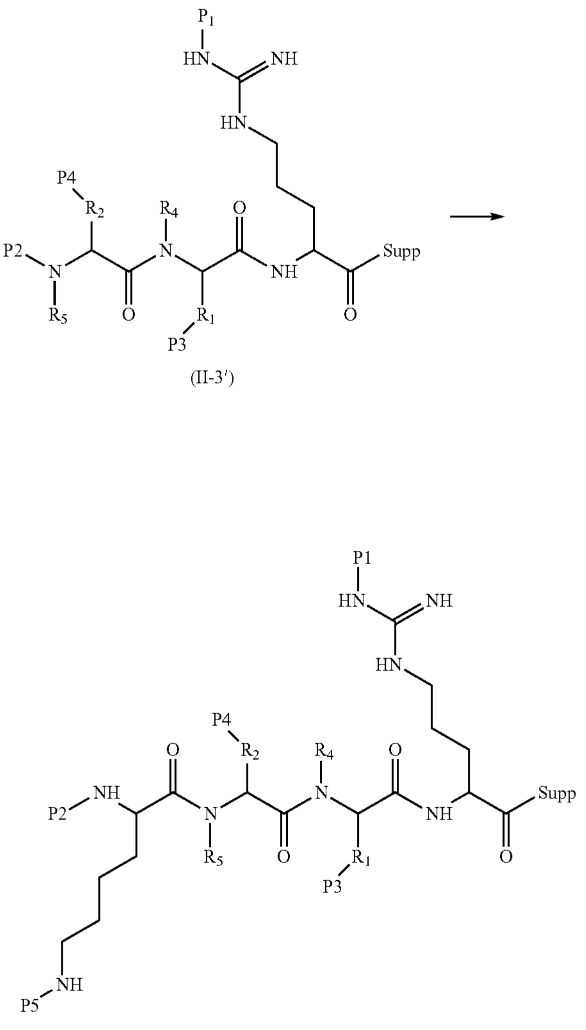

(II-3')

(II-4')

The preactivation mixture consist of 2 eq of Fmoc-Lys (Alloc)-OH (181 mg; 0.4 mmol), 2 eq of HATU (152 mg; 0.2 mmol) and 5 eq of DIPEA (169 μL; 1 mmol) dissolved in 5 mL of DMF was stirred for 1 minute, added to the resin and mixed for two hours. After this time, the resin was filtered off and washed four times (1 minute) with a fresh portion (6 ml) of DMF, and then again the Kaiser test was performed. Lack of the colour of beads indicated the completion of coupling reaction. Next, again Fmoc-deprotection and washing after Fmoc-deprotection steps were done. For monitoring of the completion of the Fmoc cleavage, the Kaiser test was made. Also in this case, the positive result of Kaiser test was obtained which allowed to proceed to the next step.

Scheme 4

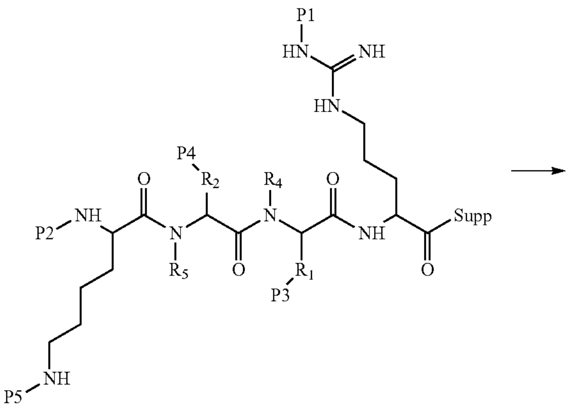

(II-4')

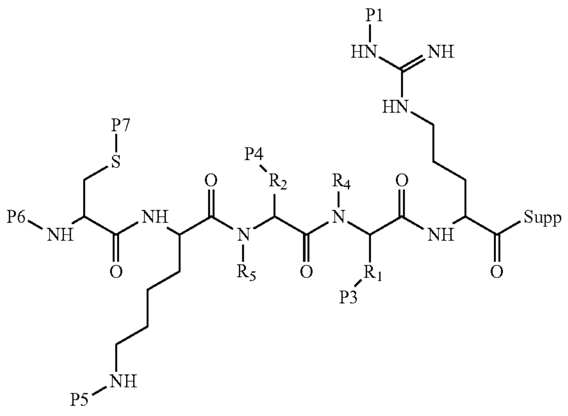

(II-5')

2 eq of Fmoc-Cys(Trt)-OH (234 mg; 0.4 mmol), 2 eq of HATU (152 mg; 0.2 mmol) and 5 eq of DIPEA (169 μL; 1 mmol) were dissolved in 5 ml of DMF—to form the preactivation mixture. After 1 minute of stirring, the mixture was added to the resin and mixed for two hours. After this time, the resin was filtered off and washed four times (1 minute) with a fresh portion (6 ml) of DMF, and then again the Kaiser test was performed. The result of Kaiser test was negative, which means the completion of the coupling reaction. Next, Alloc-deprotection step was done. The resin was filtered off and then mixed in 6 ml of dry dichloromethane (DCM) for 2 minutes, then the resin was filtered off and a mixture of 0.1 eq of $PdP(Ph_3)_4$ (23 mg; 0.02 mmol) and 20 eq of $PhSiH_3$ (481 μL; 3.9 mmol) dissolved in dry DCM was added (6 ml) and stirred for 25 minutes. Alloc-deprotection step was repeat once. For monitoring of the completion of the Alloc cleavage the Kaiser test was performed. As usual, the deep blue colour of resin and solution indicated that deprotection of amino group was completed.

Scheme 5

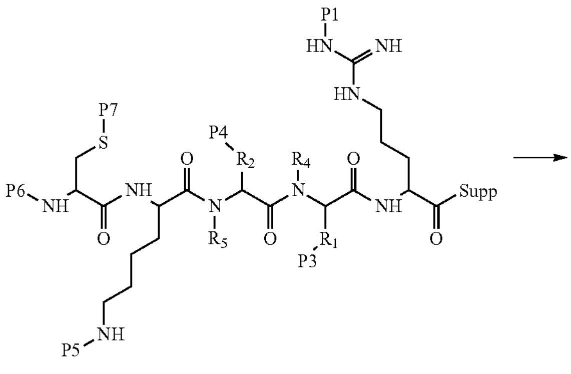

(II-5')

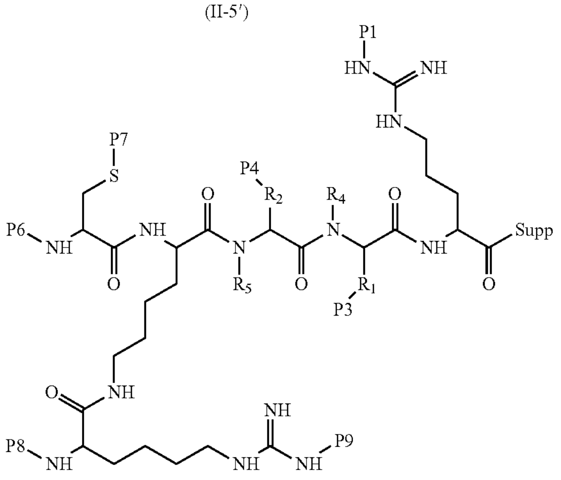

(II-6')

Next, 2 eq of Fmoc-hArg(Pbf)-OH (265 mg; 0.4 mmol), 2 eq of HATU (152 mg; 0.2 mmol) and 5 eq of DIPEA (169 μL; 1 mmol) were dissolved in 5 ml of DMF—to form the preactivation mixture. After 1 minute of stirring, the mixture was added to the resin and mixed for two hours. After this time, the resin was filtered off and washed four times (1 minute) with a fresh portion (6 ml) of DMF, and then again the Kaiser test was performed. The result of Kaiser test was negative, which means the completion of the coupling reaction. Next, again Fmoc-deprotection and washing after Fmoc-deprotection steps were done. For monitoring of the completion of the Fmoc cleavage from homoarginine and cysteine residues the Kaiser test was performed. As usual, the deep blue colour of resin and solution indicated that deprotection of amino group was completed.

Example 3: Solid Phase Synthesis of the Compound of the Formula (I) H-Lys(Cys-hArg)-Dab-ΔPro-Arg-OH, Wherein Group a is Group A2

In compound formulas illustrated in example 2, each of R1, R2, R3, R4 and R5, when present, have the same meanings as for the general definition of the compound of formula (I) specified in the present disclosure.

500 mg of pre-loaded Fmoc-L-Arg(Pbf) Wang resin with capacity 0.39 mmol/g was mixed in 6 ml of the N,N-dimethylformamide (DMF) for four hours.

Scheme 6

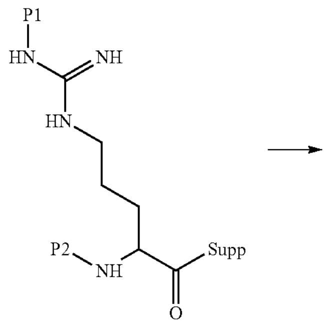

(II-1')

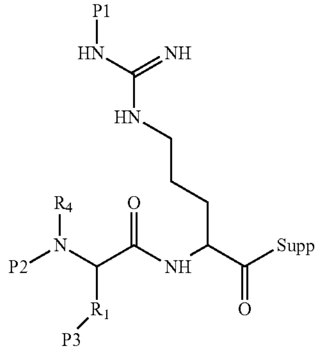

(II-2')

After that time, Fmoc-deprotection and washing after Fmoc-deprotection steps were done. After the washing, for monitoring of the completion of the Fmoc cleavage, the colorimetric assay was made. A positive Kaiser test result was obtained which allowed us to proceed to the next step. 2 eq of Fmoc-ΔPro-OH (134 mg; 0.4 mmol), 2 eq of HATU (152 mg; 0.2 mmol) and 5 eq of DIPEA (169 μL; 1 mmol) were dissolved in 5 ml of DMF—to form the preactivation mixture. The preactivation mixture was stirred for 1 minute and added to the resin and mixed for two hours. After this time the resin was filtered off and washed four times (1 minute) with DMF (6 ml) and then the acetaldehyde/chloranil test was made. A negative test result (which means the completion of the coupling reaction) was obtained which allowed us to proceed to the next step. Next, Fmoc-deprotection and washing after Fmoc-deprotection steps were done. For monitoring of the completion of the Fmoc cleavage the Kaiser test was performed. Negative result of the test allowed us to proceed to the coupling step.

Scheme 7

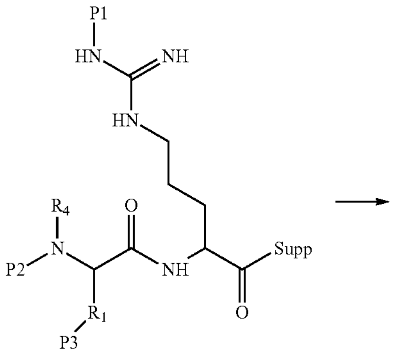

(II-2')

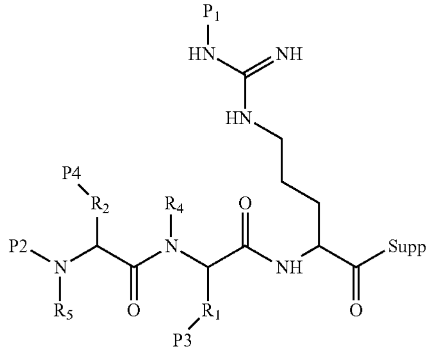

(II-3')

2 eq of Fmoc-Dab(Boc)-OH (176 mg; 0.4 mmol), 2 eq of HATU (152 mg; 0.2 mmol) and 5 eq of DIPEA (169 μL; 1 mmol) were dissolved in 5 ml of DMF. After 1 minute the preactivation mixture was added to the resin and mixed for two hours. After this time, the resin was filtered off and washed four times (1 minute) with a fresh portion (6 ml) of DMF, and then the Kaiser test was performed. The result of Kaiser test was negative, which means the completion of the coupling reaction. Next, Fmoc-deprotection and washing after Fmoc-deprotection steps were done. For monitoring of the completion of the Fmoc cleavage the Kaiser test was performed. Negative result of the test allowed us to proceed to the coupling step.

Scheme 8

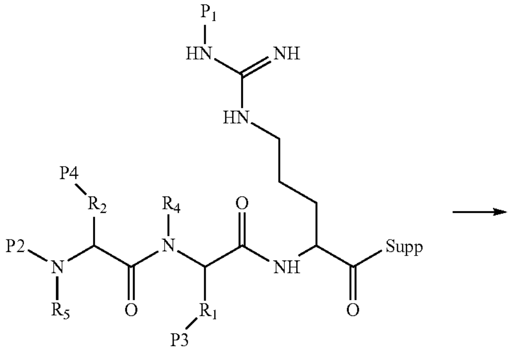

(II-3')

-continued

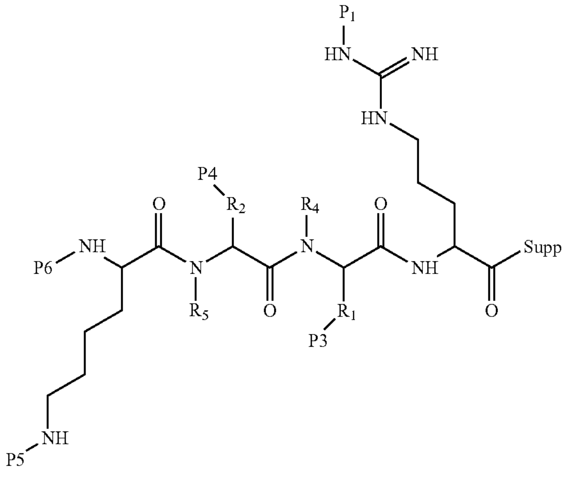

(II-6')

-continued

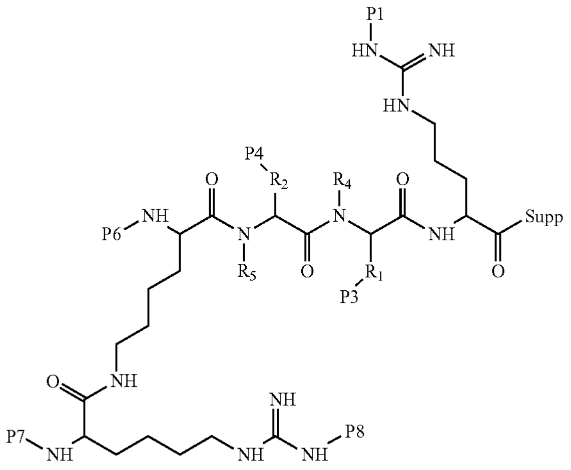

(II-7')

The preactivation mixture consist of 2 eq of Boc-Lys (Fmoc)-OH (187 mg; 0.4 mmol), 2 eq of HATU (152 mg; 0.2 mmol) and 5 eq of DIPEA (169 μL; 1 mmol) dissolved in 5 mL of DMF was stirred for 1 minute, added to the resin and mixed for two hours. After this time, the resin was filtered off and washed four times (1 minute) with a fresh portion (6 ml) of DMF, and then again the Kaiser test was performed. Lack of the colour of beads indicated the completion of coupling reaction. Next, Fmoc-deprotection and washing after Fmoc-deprotection steps were done. For monitoring of the completion of the Fmoc cleavage, the Kaiser test was made. Also in this case, the positive result of Kaiser test was obtained which allowed to proceed to the next step.

2 eq of Fmoc-hArg(Pbf)-OH (265 mg; 0.4 mmol), 2 eq of HATU (152 mg; 0.2 mmol) and 5 eq of DIPEA (169 μL; 1 mmol) were dissolved in 5 ml of DMF—to form the preactivation mixture. After 1 minute of stirring, the mixture was added to the resin and mixed for two hours. After this time, the resin was filtered off and washed four times (1 minute) with a fresh portion (6 ml) of DMF, and then again the Kaiser test was performed. The result of Kaiser test was negative, which means the completion of the coupling reaction. Next, again Fmoc-deprotection and washing after Fmoc-deprotection steps were done. For monitoring of the completion of the Fmoc cleavage from homoarginine residue the Kaiser test was performed. As usual, the deep blue colour of resin and solution indicated that deprotection of amino group was completed which allowed to proceed to the next step.

Scheme 9

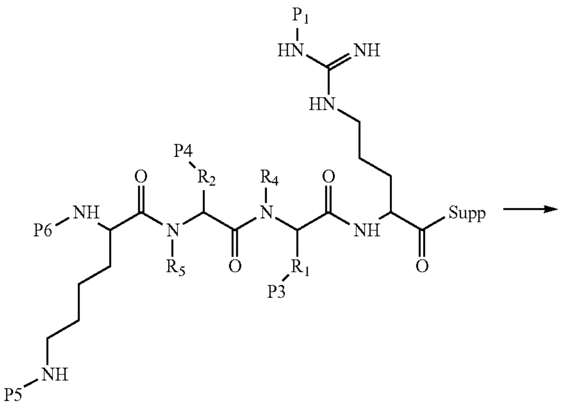

(II-6')

Scheme 10

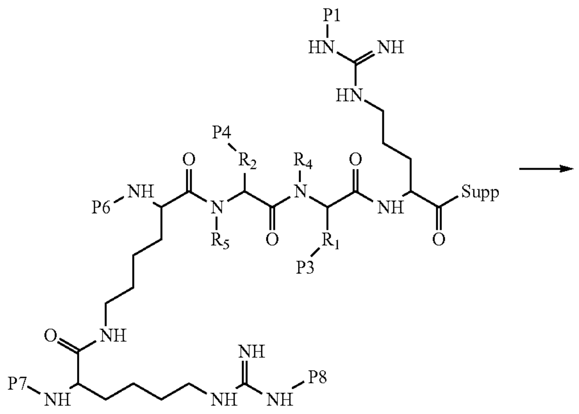

(II-7')

-continued

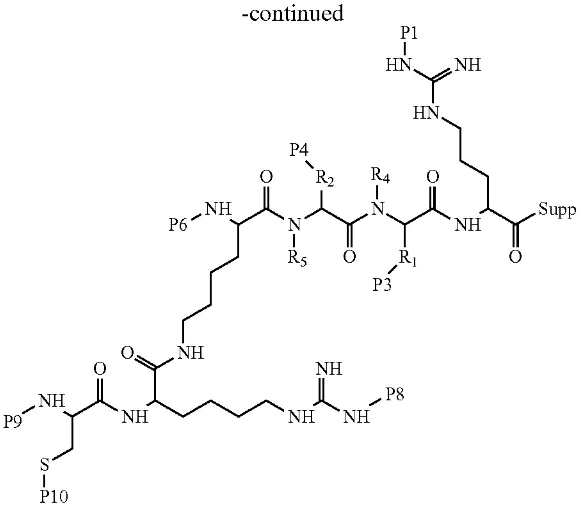

(II-8')

2 eq of Fmoc-Cys(Trt)-OH (234 mg; 0.4 mmol), 2 eq of HATU (152 mg; 0.2 mmol) and 5 eq of DIPEA (169 μL; 1 mmol) were dissolved in 5 ml of DMF—to form the preactivation mixture. After 1 minute of stirring, the mixture was added to the resin and mixed for two hours. After this time, the resin was filtered off and washed four times (1 minute) with a fresh portion (6 ml) of DMF, and then again the Kaiser test was performed. The result of Kaiser test was negative, which means the completion of the coupling reaction. Next, Fmoc-deprotection and washing after Fmoc-deprotection steps were done.

The next step of all synthesis was the washing of the peptidyl-resin with 5 mL of DCM, 5 ml of methanol (MeOH) and 5 ml of diethyl ether ($Et_2O$), three times for one minute each and subsequently the peptidyl-resin was dried under vacuum. Complete acidolytic cleavage and deprotection was occurred after 3 hours of stirring the resin in a mixture of TFA/DTT/$H_2O$/TIS in a ratio of 88:5:5:2 (v/w/v/v). Next the resin was filtered off and crude peptide was precipitated by adding the cleavage mixture dropwise into a large excess of the cold diethyl ether. Crude peptides were collected by centrifugation. Finally, the crude peptide was purified by semi-preparative high performance liquid chromatography (HPLC) using the C-12 reverse phase column. Elution was done by linear gradient 0%-20% (B) in 30 minutes where buffer (A) was 0.1% TFA in water and buffer (B) was 0.1% TFA in ACN. Pure peptide was collected, lyophilized and analysed by LC-MS. Molecular weight and elemental composition was confirmed using HRMS. All desired compounds were isolated as the trifluoroacetate salts.

Example 4: Binding of Compounds of Formula (I) to NRP-1

A. Materials and Methods

NRP-1 Binding Assay

The flat bottom surface of a 96-well plate was coated with 100 μL (200 ng/well) recombinant human NRP-1 and incubated overnight at 4° C. Non-specific binding was blocked by the incubation with 0.5% BSA in PBS. 50 μL of peptide dissolved in PBS in range concentrations and 50 μL (400 ng/mL) of human (bt)-VEGF-$A_{165}$ in PBS containing 4 μg/mL of heparin were added respectively. After 2 h incubation at room temperature the plate was washed and treated with streptavidin-horseradish peroxidase conjugate in PBS (1:8000). Chemiluminescence was quantified immediately after addition of 100 μL Chemiluminescent substrate. In a positive control only (bt)-VEGF-$A_{165}$ was present in wells, while, in negative control, wells were not coated by NRP-1. Percentages of inhibition were calculated by the following formula:

$$100\%-[[(S-SN)/(P-NS)]\cdot 100\%]$$

where S is the signal intensity measured, NS is the signal measured in negative control, and P is the signal measured in positive control.

B. Results

Active tetrapeptides described in the literature: LPPR (active part of A7R), TKPR (tuftsin) and KPRR (peptide derived from the VEGF-$A_{165}$) was modified by addition of N-terminal Cys. Obtained compounds showed significantly better affinity compared to parent sequence:

TABLE 1

Affinity comparison of active peptides with and without Cys.

| $IC_{50}$ [μM] without Cys | | Sequence | $IC_{50}$ [μM] |
|---|---|---|---|
| 80 | 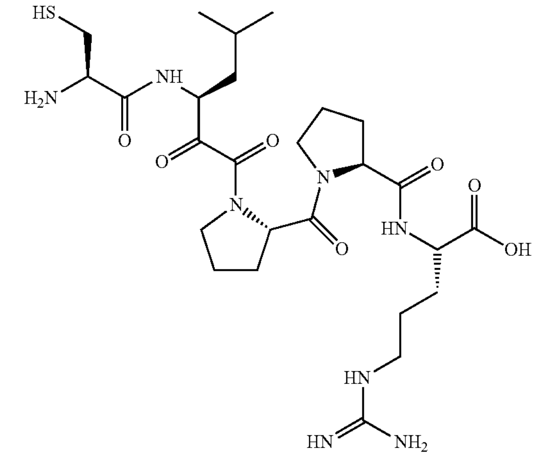 | $H_2N$-Cys-Leu-Pro-Pro-Arg-OH SEQ ID NO. 3 | 17 |

TABLE 1-continued

Affinity comparison of active peptides with and without Cys.

| $IC_{50}$ [μM] without Cys | | Sequence | $IC_{50}$ [μM] |
|---|---|---|---|
| >100 | 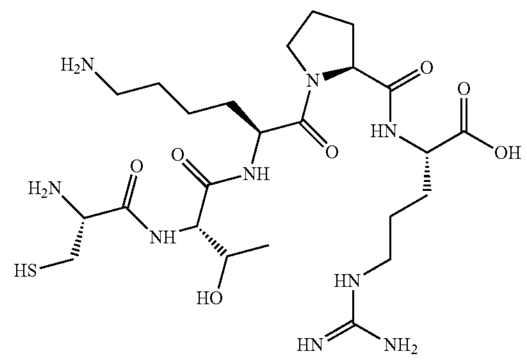 [SMILES: CC(O)[C@H](NC(=O)[C@@H](N)CS)C(=O)N[C@@H](CCCCN)C(=O)N1CCC[C@H]1C(=O)N[C@@H](CCCNC(=N)N)C(=O)O] | $H_2N$-Cys-Thr-Lys-Pro-Arg-OH SEQ ID NO. 4 | 19 |
| 4.5 | 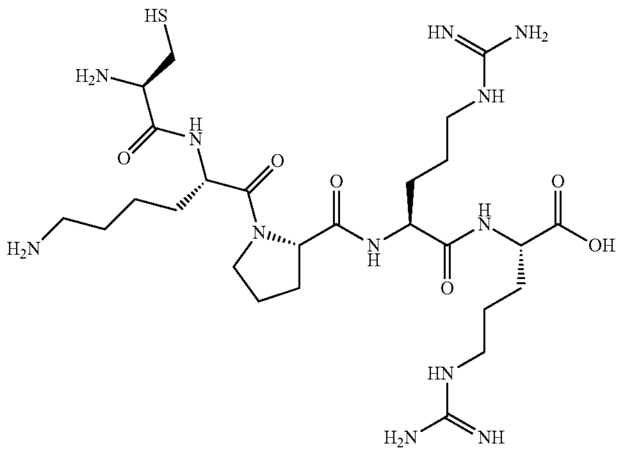 [SMILES: N=C(N)NCCC[C@H](NC(=O)[C@H](CCCNC(=N)N)NC(=O)[C@@H]1CCCN1C(=O)[C@H](CCCCN)NC(=O)[C@@H](N)CS)C(=O)O] | $H_2N$-Cys-Lys-Pro-Arg-Arg-OH SEQ ID NO. 5 | 0.10 |

Branched peptides (Lys(hArg)-X-X-Arg) without cysteine had $IC_{50}$ between 1-0.2 μM but the half maximal inhibitory concentration was obtained using less sensitive colorimetric method (Tymecka D. et al. Branched pentapeptides as potent inhibitors of the vascular endothelial growth factor 165 binding to Neuropilin-1: Design, synthesis and biological activity. *Eur J Med Chem,* 2018, Vol. 158: 453-462). Examples are showed below:

TABLE 2

Comparative peptides

| Sequence | $IC_{50}$ [μM] |
|---|---|
| H-Lys(hArg)-Pro-Pro-Arg-OH | 1.0 |
| H-Lys(hArg)-Dap-Pro-Arg-OH | 0.2 |
| H-Lys(hArg)-Dab-Pro-Arg-OH | 0.2 |
| H-Lys(hArg)-Pro-Dab-Arg-OH | 0.2 |

Selected active branched peptides were tested again using a more sensitive method with chemiluminescent detection. Moreover, some modified compounds were also examined. The $IC_{50}$ for selected Lys(hArg)-X-X-Arg peptides was between 2-21 μM (Puszko A. K. at al. Neuropilin-1 peptide-like ligands with proline mimetics, tested using the improved chemiluminescence affinity detection method. MedChemComm, 2019, Vol. 10: 332-340). Some examples are showed below:

TABLE 3

Further comparative peptides

| Sequence | $IC_{50}$ [μM] |
|---|---|
| H-Lys(hArg)-Pro-Pro-Arg-OH | 20.9 |
| H-Lys(hArg)-ΔPro-ΔPro-Arg-OH | 14.0 |
| H-Lys(hArg)-Oic-Oic-Arg-OH | 7.2 |
| H-Lys(hArg)-Dab-Pro-Arg-OH | 8.9 |
| H-Lys(hArg)-Dab-ΔPro-Arg-OH | 4.3 |
| H-Lys(hArg)-Dab-Oic-Arg-OH | 2.3 |

Addition of cysteine to the N-terminal of the sequence caused 100-fold decrease in $IC_{50}$ value. Some examples are showed below:

TABLE 4
| Peptides of formula (I) | | |
|---|---|---|
| Structure | Sequence | $IC_{50}$ [nM] |
| 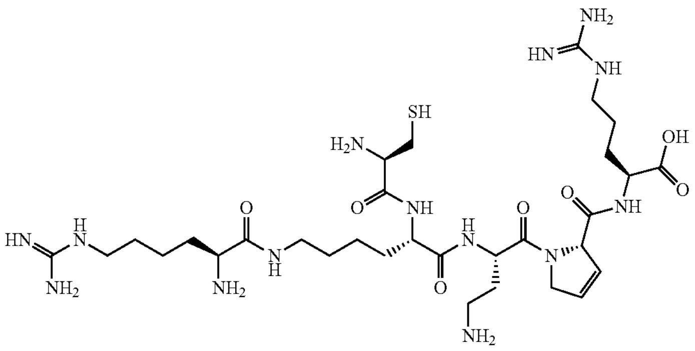 [SMILES: N=C(N)NCCCC[C@H](N)C(=O)NCCCC[C@H](NC(=O)[C@@H](N)CS)C(=O)N[C@@H](CCN)C(=O)N1CC=C[C@H]1C(=O)N[C@@H](CCCNC(=N)N)C(=O)O] | H-Cys-Lys(hArg)-Dab-ΔPro-Arg-OH SEQ ID NO. 6 | 70 |
| 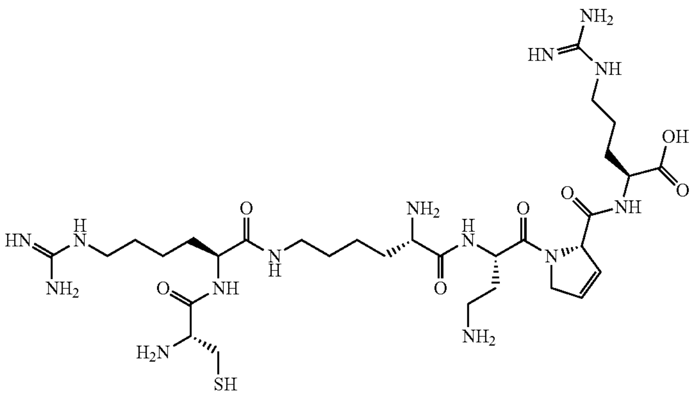 [SMILES: N=C(N)NCCCC[C@H](NC(=O)[C@@H](N)CS)C(=O)NCCCC[C@H](N)C(=O)N[C@@H](CCN)C(=O)N1CC=C[C@H]1C(=O)N[C@@H](CCCNC(=N)N)C(=O)O] | H-Lys(Cys-hArg)-Dab-ΔPro-Arg-OH SEQ ID NO. 7 | 60 |
| 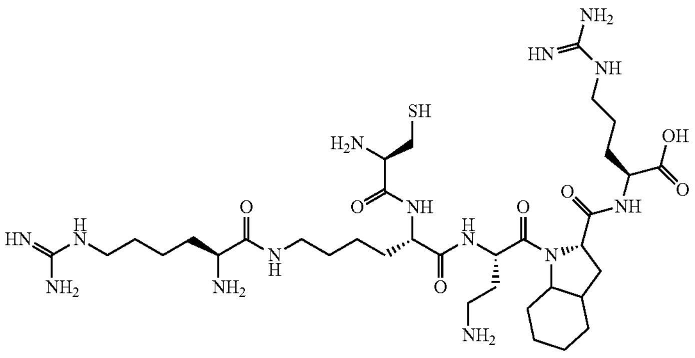 | H-Cys-Lys(hArg)-Dab-Oic-Arg-OH SEQ ID NO. 8 | 50 |
| 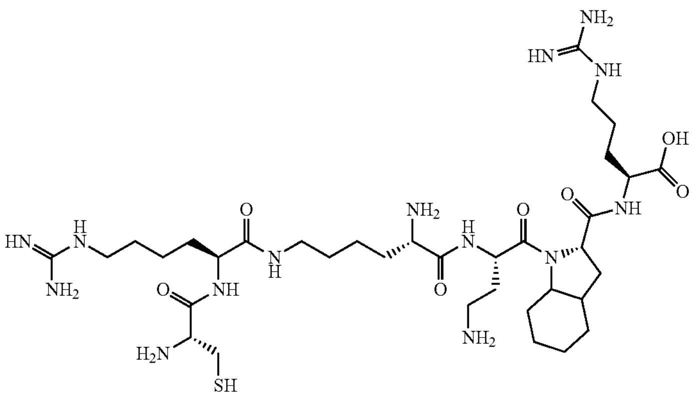 | H-Lys(Cys-hArg)-Dab-Oic-Arg-OH SEQ ID NO. 9 | 40 |

The invention claimed is:

1. A compound of formula (I) below:

(I)

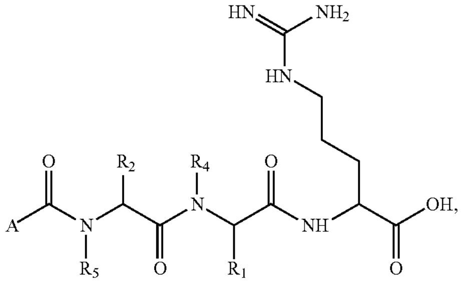

wherein, for groups R1 and R4, a) R1 is a group of formula (LC1)

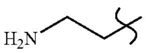

and R4 is H, or b) R1 and R4, together with the carbon and nitrogen atoms to which they are linked, form a pyrrolidinyl ring, or c) R1 and R4, together with the carbon and nitrogen atoms to which they are linked, form a 2,5-dihydro-1-H-pyrrolyl ring, or d) R1 and R4, together with the carbon and nitrogen atoms to which they are linked, form a octahydro-1H-indolyl ring, or e) R1 is a group of formula (LC2)

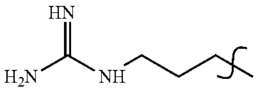

and R4 is H, for groups R2 and R5, a) R2 is a group of formula (LC3)

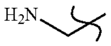

and R5 is H, or b) R2 is a group of formula (LC1)

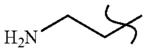

and R5 is H, or c) R2 and R5, together with the carbon and nitrogen atoms to which they are linked, form a pyrrolidinyl ring, or d) R2 and R5, together with the carbon and nitrogen atoms to which they are linked, form a 2,5-dihydro-1-H-pyrrolyl ring, or e) R2 and R5, together with the carbon and nitrogen atoms to which they are linked, form a octahydro-1H-indolyl ring, or f) R2 is a group of formula (LC2)

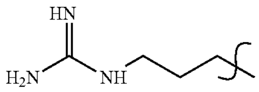

and R5 is H, or g) R2 is a group of formula (LC4)

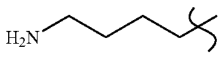

and R5 is H,

A is selected in the group of formulas A1 and A2 below:

wherein A1 is of the formula:

(A1)

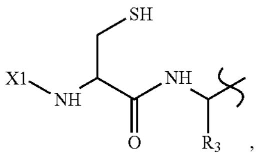

, wherein X1 is selected in the group consisting of H, —C(=O)—CH3 and an amine protecting group, and wherein R3 is selected in the group consisting of a) R3 is a group of formula (LC4)

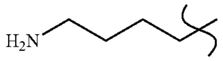

, or b) R3 is a group of formula (LC5)

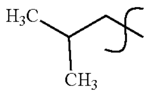

, or c) R3 is a group of formula (LC6)

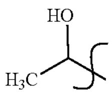

, or d) R3 is a group of formula (LC7)

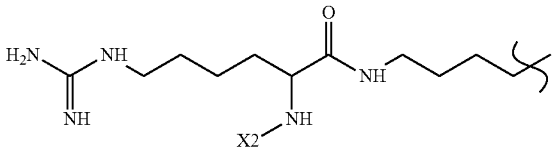

, and wherein X2 is selected in the group consisting of H, —C(=O)—CH3 and an amine protecting group, and wherein A2 is of the formula below:

(A2)

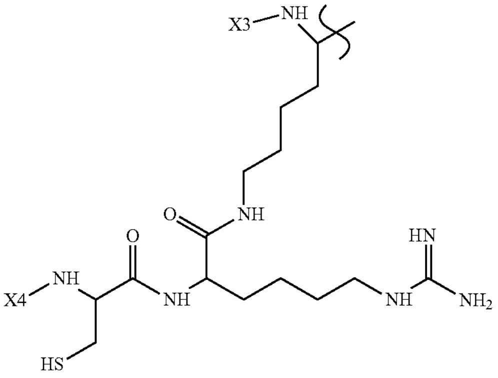

wherein X3 and X4, which are identical or different, and are selected from the group consisting of H, —C(=O)—CH3 and an amine protecting group, provided that the compound of formula (I) does not consist of the peptide CKPPR or CTKPR, and pharmaceutically acceptable salts and/or racemic, enantiomeric, diastereoisomeric or tautomeric forms thereof.

2. The compound of formula (I) according to claim 1, wherein A is A1, and R3 is a group of formula (LC7)

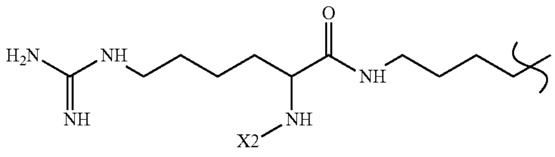

, and R1, R2, R4, R5, X1 and X2 are as defined in claim 1.

3. The compound of formula (I) according to claim 1, wherein A is A1 and R1 and R4, together with the carbon and nitrogen atoms to which they are linked, form a 2,5-dihydro-1-H-pyrrolyl ring, and R2, R3, R5, X1 and X2 are as defined in claim 1.

4. The compound of formula (I) according to claim 1, wherein group A is A1, wherein R1 and R4, together with the carbon and nitrogen atoms to which they are linked, form a octahydro-1H-indolyl ring, and R2, R3, R5, X1 and X2 are as defined in claim 1.

5. The compound of formula (I) according to claim 1, wherein group A is A1, wherein R2 is a group of formula (LC1)

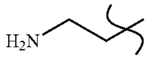

and R5 is H, and R1, R3, R4, X1 and X2 are as defined in claim 1.

6. The compound of formula (I) according to claim 1, wherein group A is A1, wherein R1 and R4, together with the carbon and nitrogen atoms to which they linked, form a octahydro-1H-indolyl [Oic] ring, R2 is a group of formula (LC1)

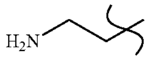

and R5 is H, R3 is a group of formula (LC7)

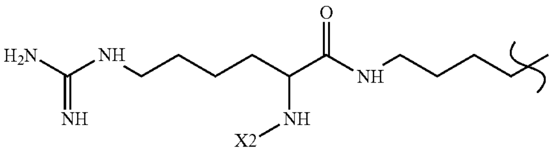

and wherein X1 and X2 are as defined in claim 1.

7. The compound of formula (I) according to claim 1, wherein group A is A2 wherein R1 and R4, together with the carbon and nitrogen atoms to which they linked, form a 2,5-dihydro-1-H-pyrrolyl [ΔPro], and R2, R5 and X3 and X4 are as defined in claim 1.

8. The compound of formula (I) according to claim 1, wherein group A is A2, wherein R2 is a group of formula (LC1)

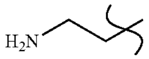

and R5 is H, [Dab], and R1, R4 and X3, and X4, are as defined in claim 1.

9. The compound of formula (I) according to claim 1, wherein group A is A2, wherein R1 and R4, together with the carbon and nitrogen atoms to which they linked, form a 2,5-dihydro-1-H-pyrrolyl [ΔPro], R2 is a group of formula (LC1)

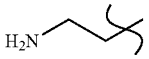

and R5 is H, [Dab], and X3, and X4 are as defined I claim 1.

10. The compound of formula (I) according to claim 1, having the formula (I-A) below:

(I-A)

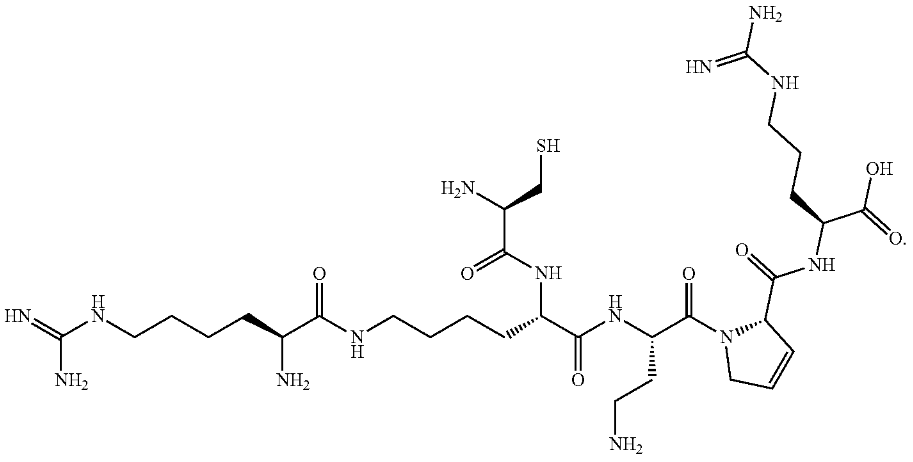

(SEQ ID NO: 6)

11. The compound of formula (I) according to claim 1, having the formula (I-B) below:
(I-B)
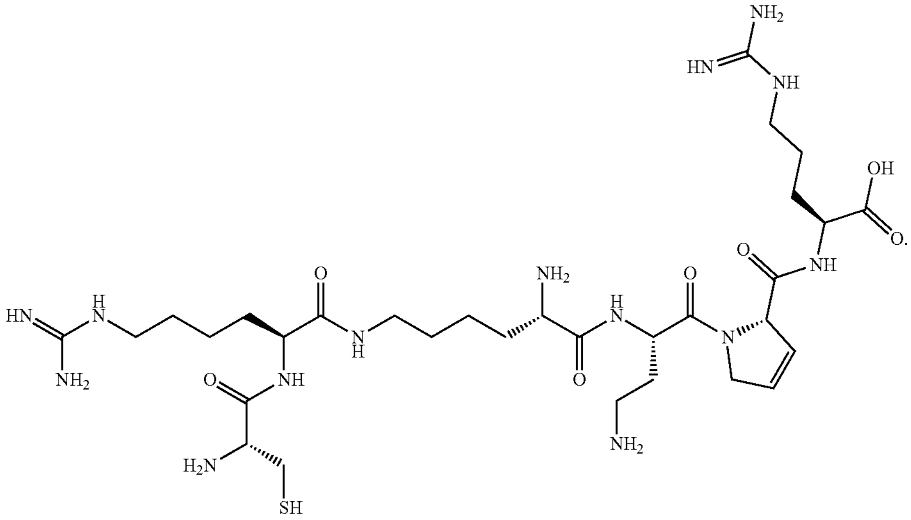
(SEQ ID NO: 7)
12. The compound of formula (I) according to claim 1, having the formula (I-C) below:
(I-C)
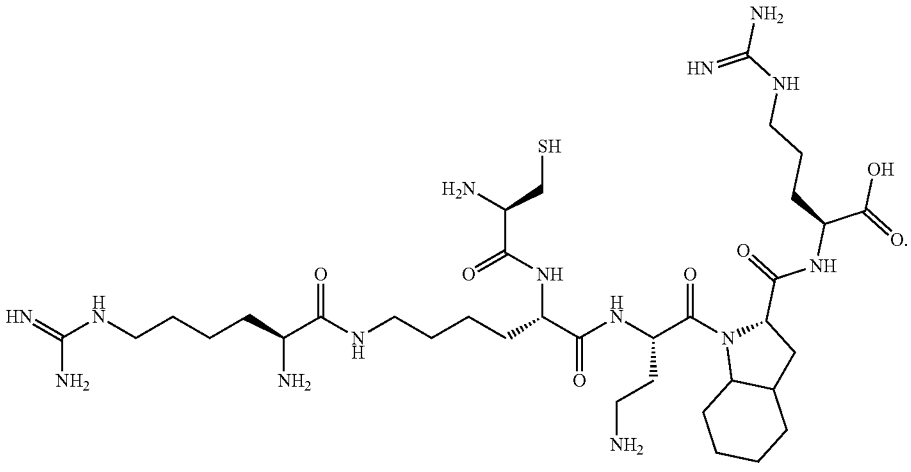
(SEQ ID NO: 8)

13. The compound of formula (I) according to claim 1, having the formula (I-D) below:

(I-D)

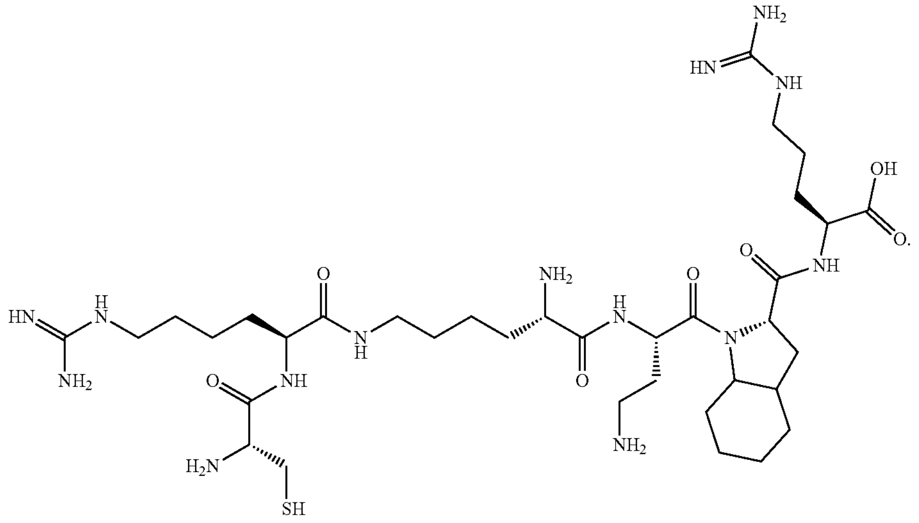

(SEQ ID NO: 9)

14. A pharmaceutical composition comprising a compound of formula (I) as defined in claim 1.

15. A method for treating breast cancer in a subject in need thereof, comprising administering to the subject a therapeutically effective amount of the compound of formula (I) according to claim 1, or a pharmaceutically acceptable salt and/or racemic, enantiomeric, diastereoisomeric or tautomeric form thereof.

* * * * *

SEQUENCE LISTING

<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: Synthetic A7R

<400> SEQUENCE: 1

Ala Thr Trp Leu Pro Pro Arg
1 5

<210> SEQ ID NO 2
<211> LENGTH: 4
<212> TYPE: PRT
<213> ORGANISM: Artificial Sequence
<220> FEATURE:
<223> OTHER INFORMATION: Synthetic general sequence of peptides exhibiting VEGF165/NRP-1 binding inhibitory effect
<220> FEATURE:
<221> NAME/KEY: VARIANT
<222> LOCATION: 1
<223> OTHER INFORMATION: Xaa in position 1 represents a lysine(homoarginine), where the epsilon amine group of Lys forms amide bond with homoarginine (hArg) carboxyl group

<400> SEQUENCE: 2

Xaa Pro Pro Arg
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Comparative peptide

<400> SEQUENCE: 3

Cys Leu Pro Pro Arg
1 5

<210> SEQ ID NO 4
<211> LENGTH: 5
<212> TYPE: PRT
<213> ORGANISM: Artificial Sequence
<220> FEATURE:
<223> OTHER INFORMATION: Synthetic comparative sequence

<400> SEQUENCE: 4

Cys Thr Lys Pro Arg
1 5

<210> SEQ ID NO 5
<211> LENGTH: 5
<212> TYPE: PRT
<213> ORGANISM: Artificial Sequence
<220> FEATURE:
<223> OTHER INFORMATION: Synthetic comparative sequence

<400> SEQUENCE: 5

Cys Lys Pro Arg Arg
1 5

<210> SEQ ID NO 6
<211> LENGTH: 5
<212> TYPE: PRT
<213> ORGANISM: Artificial Sequence -continued
<220> FEATURE:
<223> OTHER INFORMATION: Synthetic branched peptide of the invention
<220> FEATURE:
<221> NAME/KEY: VARIANT
<222> LOCATION: 2
<223> OTHER INFORMATION: Xaa in position 2 represents a lysine(homoarginine), where the epsilon amine group of Lys forms amide bond with homoarginine (hArg) carboxyl group
<220> FEATURE:
<221> NAME/KEY: VARIANT
<222> LOCATION: 3
<223> OTHER INFORMATION: Xaa in position 3 represents a 2,4 diaminobutyric acid
<220> FEATURE:
<221> NAME/KEY: VARIANT
<222> LOCATION: 4
<223> OTHER INFORMATION: Xaa in position 4 represents a 3,4 dehydroproline

<400> SEQUENCE: 6

Cys Xaa Xaa Xaa Arg
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic branched peptide of the invention
<220> FEATURE:
<221> NAME/KEY: VARIANT
<222> LOCATION: 1
<223> OTHER INFORMATION: Xaa in position 1 represents a lysine substituted with a cystein linked to an homoarginine
<220> FEATURE:
<221> NAME/KEY: VARIANT
<222> LOCATION: 2
<223> OTHER INFORMATION: Xaa in position 2 represents a 2,4 diaminobutyric acid
<220> FEATURE:
<221> NAME/KEY: VARIANT
<222> LOCATION: 3
<223> OTHER INFORMATION: Xaa in position 3 represents a 3,4 dehydroproline

<400> SEQUENCE: 7

Xaa Xaa Xaa Arg
1

<210> SEQ ID NO 8
<211> LENGTH: 5
<212> TYPE: PRT
<213> ORGANISM: Artificial Sequence
<220> FEATURE:
<223> OTHER INFORMATION: Synthetic branched peptide of the invention
<220> FEATURE:
<221> NAME/KEY: VARIANT
<222> LOCATION: 2
<223> OTHER INFORMATION: Xaa in position 2 represents a lysine(homoarginine), where the amine group of Lys forms amide bond with homoarginine (hArg) carboxyl group
<220> FEATURE:
<221> NAME/KEY: VARIANT
<222> LOCATION: 3
<223> OTHER INFORMATION: Xaa in position 3 represents a 2,4 diaminobutyric acid
<220> FEATURE:
<221> NAME/KEY: VARIANT
<222> LOCATION: 4
<223> OTHER INFORMATION: Xaa in position 4 represents a 1H-indole-2-carboxylic acid

<400> SEQUENCE: 8

Cys Xaa Xaa Xaa Arg

-continued

```
1               5


<210> SEQ ID NO 9
<211> LENGTH: 4
<212> TYPE: PRT
<213> ORGANISM: Artificial Sequence
<220> FEATURE:
<223> OTHER INFORMATION: Synthetic branched peptide of the invention
<220> FEATURE:
<221> NAME/KEY: VARIANT
<222> LOCATION: 1
<223> OTHER INFORMATION: Xaa in position 1 represents a lysine
      substituted with a cystein linked to an homoarginine
<220> FEATURE:
<221> NAME/KEY: VARIANT
<222> LOCATION: 2
<223> OTHER INFORMATION: Xaa in position 2 represents a 2,4
      diaminobutyric acid
<220> FEATURE:
<221> NAME/KEY: VARIANT
<222> LOCATION: 3
<223> OTHER INFORMATION: Xaa in position 3 represents a 1H-indole-2-
      carboxylic acid

<400> SEQUENCE: 9

Xaa Xaa Xaa Arg
1
```